United States Patent

Stratbucker

(10) Patent No.: US 6,327,487 B1
(45) Date of Patent: *Dec. 4, 2001

(54) BIOELECTRIC INTERFACE

(76) Inventor: Robert A. Stratbucker, 7125 Country Club, Omaha, NE (US) 68152

(*) Notice: Subject to any disclaimer, the term of this patent is extended or adjusted under 35 U.S.C. 154(b) by 0 days.

This patent is subject to a terminal disclaimer.

(21) Appl. No.: 09/374,873

(22) Filed: Aug. 16, 1999

Related U.S. Application Data

(63) Continuation-in-part of application No. 08/885,690, filed on Jun. 30, 1997, now Pat. No. 5,938,597, which is a continuation-in-part of application No. 08/434,658, filed on May 4, 1995, now Pat. No. 5,678,545.
(60) Provisional application No. 60/103,162, filed on Oct. 6, 1998.

(51) Int. Cl.⁷ ............................. A61B 5/0408; A61N 1/04
(52) U.S. Cl. ..................... 600/382; 600/390; 600/391; 600/393; 607/149; 607/152
(58) Field of Search ............ 600/382, 388–391, 600/393; 607/148, 149, 152

(56) References Cited

U.S. PATENT DOCUMENTS

| | | | |
|---|---|---|---|
| 3,612,061 | 10/1971 | Collins | 128/418 |
| 3,993,049 * | 11/1976 | Kater | 600/391 |
| 4,067,342 * | 1/1978 | Burton | 607/152 |
| 4,121,575 | 10/1978 | Mills et al. | 128/2.06 |
| 4,209,481 | 6/1980 | Kashiro et al. | 264/24 |
| 4,328,814 | 5/1982 | Arkans | 128/640 |
| 4,416,274 * | 11/1983 | Jacobsen et al. | 604/20 |
| 4,465,074 * | 8/1984 | Buchalter | 600/397 |
| 4,524,087 | 6/1985 | Engel | 427/2 |
| 4,583,549 | 4/1986 | Manoli | 128/640 |
| 4,706,680 | 11/1987 | Kuesch et al. | 128/640 |
| 4,778,635 | 10/1988 | Hechtman et al. | 264/24 |
| 4,955,381 | 9/1990 | Way et al. | 128/419 |
| 4,957,109 | 9/1990 | Groeger et al. | 128/640 |
| 4,989,607 | 2/1991 | Kuesch et al. | 128/640 |
| 5,045,249 | 9/1991 | Jin et al. | 264/24 |
| 5,063,932 | 11/1991 | Dahl et al. | 128/639 |
| 5,080,099 | 1/1992 | Way et al. | 128/640 |
| 5,124,107 | 6/1992 | Schmid | 264/255 |
| 5,132,058 | 7/1992 | Suyama et al. | 264/24 |
| 5,143,071 | 9/1992 | Keusch et al. | 128/640 |
| 5,184,620 | 2/1993 | Cudahy et al. | 128/639 |
| 5,191,886 | 3/1993 | Paeth et al. | 128/640 |
| 5,232,639 | 8/1993 | Reitz et al. | 264/22 |
| 5,289,822 | 3/1994 | Highe et al. | 128/640 |
| 5,295,482 | 3/1994 | Clare et al. | 128/639 |
| 5,327,888 | 7/1994 | Imran | 128/640 |
| 5,331,959 | 7/1994 | Imran | 128/639 |
| 5,678,545 | 10/1997 | Stratbucker | 128/640 |
| 5,938,597 * | 8/1999 | Stratbucker | 600/382 |
| 6,134,480 * | 10/2000 | Minogue | 600/391 |

* cited by examiner

*Primary Examiner*—Lee Cohen
(74) *Attorney, Agent, or Firm*—James D. Welch

(57) ABSTRACT

Disclosed is a bioelectric interface containing at least two electrodes and which is characterized as a support sheet with such attributes as an undulated outer edge, and/or with holes therethrough which allow access to a subject's ski in use, and/or with perforations therein which allow easy detaching and deployment of electrodes therefrom is disclosed. The preferred version has all electrodes necessary to perform twelve lead ECG monitoring. The bioelectric interface includes an adhesive sheet in functional combination with the support sheet, which adhesive sheet simultaneously presents with, preferably, scrim and/or slit effected essentially anisotropic specific impedance properties in combination with essentially isotropic mechanical pliability and adhesion properties. The electrodes are affixed to the support sheet in a manner such that their relative positions with respect to one another are essentially fixed. The present invention also provides for spring-loaded electrode contact improving access.

27 Claims, 10 Drawing Sheets

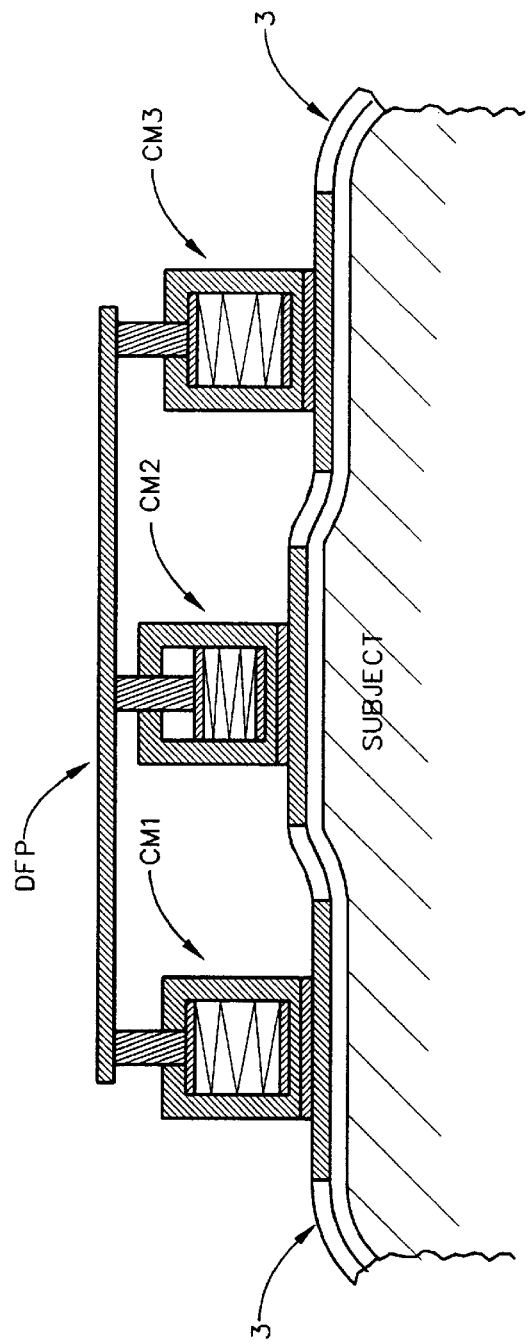

BIOELECTRIC INTERFACE

This Application is a CIP of patent application Ser. No. 08/885,690 filed Jun. 30, 1997, now U.S. Pat. No. 5,938,597, which was a CIP of patent application Ser. No. 08/434,658 filed May 4, 1995, (now U.S. Pat. No. 5,678,545), and is further a CIP of Provisional Application No. 60/103,162 filed Oct. 6, 1998.

It is also disclosed that a (EPO) Application, Ser. No. 97308319.9 was filed Oct. 20, 1997 and corresponds to U.S. application Ser. No. 08/434,658 filed May 4, 1995, without priority being claimed therefrom.

TECHNICAL FIELD

The present invention relates to systems of electrodes for use in bioelectric interfacing. More particularly, the present invention provides a support sheet secured plurality of appropriately positioned electrodes for simultaneous application to a subject, and provides for use of a scrim-based electrically anisotropic hydropolymer system, the presence of an undulated outer edge, subject accessing holes therethrough, and perforations for enabling easy detaching and deploying of containing electrodes.

BACKGROUND

Conventional medical analysis and therapy often involves use of a plurality of individual electrodes, each applied independently to an appropriate location on a subject's body by way of electrically conductive paste, and securing means such as a skin compatible adhesive. A relevant example of use is in the monitoring of Electrocardiogram (ECG) signals at precordial; and at left and right arm, and left Leg locations by independent electrodes in an Einthoven triangle configuration.

Further, it is known to apply individual non-invasive precordial electrodes to a subject's chest to allow not only the acquiring of ECG data, but to allow defibrillation of fibrillating hearts and to allow the pacing of arrested hearts and the like.

A problem which presents in the use of such independent electrodes, however, is that reliable, repeatable placement upon a subject's body is difficult. For instance, it is generally accepted that a majority of the errors encountered in acquiring ECG data is caused by improper electrode placement by medical technical staff.

Of relatively recent development are flexible electrode pads which comprise a multiplicity of electrodes affixed thereto in an appropriate pattern for use in medical analysis and/or therapy. For instance, a Patent to Manoli, U.S. Pat. No. 4,583,549 describes an ECG electrode pad in which six conductive discs are plated and etched on a flexible adhesive pad in a clinically conventional predetermined pattern effective for precordial ECG electrode placement. Reproducible attachment of said six electrodes to a subject's chest in the proper arrangement for use with standard ECG machines is thus made possible by a single application of an electrode pad of an appropriate size for use with any subject. However, it would seem that the Manoli system would require a host of numerous sized electrode pads to accommodate subjects of different sizes as the Claims recite rather strict electrode placement criteria which are referred with respect to a subject's body. A single electrode pad would not meet said requirements on subjects of different sizes. A Patent, U.S. Pat. No. 4,121,575 to Mills et al. describes a multiple electrode device for application to a subject's chest, formed in stretchable non-conductive material having apertures in the V1–V6 positions. The capability for stretching the material is held to allow accurate positioning of V1–V6 electrodes on subjects of differing body size. A Patent to Groeger et al., U.S. Pat. No. 4,957,109 describes an electrode assembly comprising right and left arm and leg leads, and precordial leads all affixed to a common structure. The arm and leg leads do not affix to a subject's chest during use. The Mills et al. and Groeger et al. systems do not serve to maintain a relatively fixed positioning of electrodes therein during use, and it is noted that movement between electrodes during use frequently causes confounding noise generation in electrocardiography systems. Another Patent, U.S. Pat. No. 5,327,888 to Imran describes a precordial electrode strip which is supplied with detachable RA, LA and LL limb leads, which detachable limb leads are applied to subject limbs in use.

Patents to Way et al., U.S. Pat. Nos. 4,955,381 and 5,080,099 describe multiple conductive polymer pad containing electrodes for performing multiple electrical physiological functions from a set of electrodes with respect to a subject, at or about the same time, such as defibrillation, pacing and monitoring. Other Patents which disclose multiple electrode assemblies are U.S. Pat. No. 4,328,814 to Arkans and U.S. Pat. No. 5,191,886 to Paeth et al. These Patents each describe a plurality of electrodes configured in a physically seriesed configuration with conductive leads to various physically seriesed contacts, present at one end thereof. In addition, a Patent to Collins, U.S. Pat. No. 3,612,061 describes a porous sheet of elastic material which supports an array of electrodes adapted to contact a wearer's skin, and U.S. Pat. No. 5,184,620 to Cudahy et al. describes an electrode pad system comprises of a multiplicity of electrodes which are utilized in defibrillation and pacing scenarios as directed by an on-line computer driven analysis and electrical energy application system, which system distributes electrical energy to appropriate sets of said multiplicity electrodes in response to subject needs.

Continuing, it is to be understood that particularly appropriate materials in which to form an electrode pad with a plurality of ECG monitoring electrodes present therein are hydropolymers. This is because hydropolymers can be pliable, self-adhesive and compatible with maintaining the requisite hydration of subject skin to which they affix during prolonged use. The pliable property makes hydropolymers exceptionally well suited for application to unpredictable irregularities of various subject's chests and the self-adhesive property negates the need to apply adhesive material to affix the present invention to a subject's body during uses. As well, the need to apply electrically conductive paste to electrically conducting areas of electrodes becomes unnecessary.

A Patent, U.S. Pat. No. 5,331,959 to Imran, describes a low impedance dry conforming contact member in which are present rods or filaments which are cured into material such as a silicon-based material, such that when configured as an electrode provide impedance reducing projections which protrude into the pores of a subject's skin during use. Said rods or filaments reduce the need to use conductive paste. Another Patent, U.S. Pat. No. 4,524,087 to Engel, describes a conductive electrode application comprising an adhesive, swellable, dermally-nonirritating, conformable, ionic hydropolymer biomedical electrode fabricated by a claimed process.

Continuing, three Patents to Keusch et al., U.S. Pat. Nos. 4,706,680, 4,989,607 and 5,143,071 describes hydrogels which are caused to be highly conductive by the inclusion of an essentially uniformly distributed active electrolyte therein. Said Patents state that to form the hydrogels a polymeric mixture is caused to become cross-linked by exposure to radiant energy. This causes a gel-like solid to form which is sufficiently tacky and adhesive to adhere to subject's skin and which is substantially non-stringy and non-aggressive so that subject comfort is protected.

A Patent to Highe et al., U.S. Pat. No. 5,289,822 describes an electrode formed of a dry-conductive material having an outer surface for placement in contact with a subject's skin. A composition is deposited on at least a portion of the surface of the dry-electrode which comprises a plurality of water-containing vesicles. The purpose of said water-containing vesicles being to effect an immediate lowering of subject skin resistance upon the application of the electrode. It is stated that a period of approximately four minutes is otherwise required for moisture from a subject's skin to naturally occur at the electrode.

A Patent to Schmid, U.S. Pat. No. 5,124,107 describes a process for manufacturing a body electrode which comprises one or more galvanically active sensors which are combined with a first layer capable of adhering to a subject's skin, on a body contact side thereof. A second covering or supporting layer is also present on the opposite side of the body electrode. The process for manufacture provides that the two layers are sequentially cast in a mold which provides intended shape and size. The procedure avoids manufacturing problems encountered where electrodes are stamped from a preformed sheet. A potential problem of using such an electrode as provided by the Schmid 107 Patent is that it provides a laterally oriented conductive path between said galvanically active sensors through the first layer thereof. Electrically anisotropic conducting hydropolymers would be preferable.

Continuing, a Patent to Suyama et al, U.S. Pat. No. 5,132,058 describes a process for producing an anisotropically electroconductive sheet having a plurality of electroconductive portions extending in the direction of the thickness of the sheet. Application of an anisotropic magnetic field is utilized to draw electroconductive particles into a molding material such that said electroconductive particles gather where said electromagnetic field is applied. Another Patent which describes a similar system to that achieved by practice of the Suyama et al. Patent is U.S. Pat. No. 4,778,635 to Hechtman et al. A Patent to Kashiro et al., U.S. Pat. No. 4,209,481 describes an anisotropically electroconductive sheet in which electroconductive wires are formed into patterned groupings, which patterned groupings are in turn formed into patterns. The wires are parallel in the direction of the sheet thickness, and spaced apart by non-electroconductive elastomer. Another Patent, U.S. Pat. No. 5,045,249 to Jin et al., describes electrical interconnections made by means of a layer or sheet medium comprising chains of magnetically aligned, electrically conductive particles in a nonconducting medium. End particles of chains protrude from a surface of the medium to effect electrical contact. A Patent to Abraham et al. describes an electrode for use with electrosurgical apparatus which provides capacitive coupling with the skin of a subject. The electrode includes a conductive plate connected to the electrosurgical apparatus with an insulating layer disposed in contact with the conductive plate and on the opposite face of the insulator there is provided conductive material in the form of a plurality of discrete islands of conductive adhesive material which contact the skin of a subject during use. Another Patent, U.S. Pat. No. 5,232,639 to Reitz et al. describes a process for forming articles with anisotropic void distributions therein.

It is also established that electrode configuration can be important in determining the accuracy of monitored signals. For instance, the use of a Bulls-eye shaped electrode, which comprises a central electrode surrounded by one or more annular ring electrodes, can provide signals which focus upon a specific region of a subject's heart, which focus is not available when a simple electrode geometry is utilized. As well, Bulls-eye shaped electrodes allow determination of derivatives of detected signals in use.

An article be He et al. titled "Body Surface Laplacian Mapping of Cardiac Electrical Activity" published in The American J. of Cardiology, Vol. 70, Dec. 15, 1992 describes the use of Bulls-eye shaped electrodes to map derivatives of cardiogenic signals.

Patents which describe unusual geometrical electrode configurations are, for instance, a Patent to Clare et al., U.S. Pat. No. 5,295,482 which discloses a large surface area electrode in which a central portion is surrounded by two surrounding ring portions., said central and two surrounding ring portions being separated from one another by annular regions. This Patent states that during use current density is found to be greater at the outer edge of an electrode than it is at a more central location. The purpose of the described system is disclosed as being to effect a more uniform distribution of current density over the effective large surface area of the disclosed electrode during use, by providing multiple "outer-edge" providing portions. Other reference which describes the "edge-effect" are a Patent to Dahl et al., U.S. Pat. No. 5,063,932 and a Canadian Patent No. 1,219, 642. In addition, two articles also treat the subject, said articles being: "Optimal Electrode Designs for Electrosurgery, Defibrillation, and External Cardiac Pacing", by Kim et al., which appeared in Transactions On Biomedical Engineering, Vol. BME-33, No. 9, September 1986; and "Analysis and Control of the Dispersive Current Distribution under Circular Dispersive Electrodes", by Wiley and Webster, which appeared in the IEEE Transactions On Biomedical Engineering, Vol. BME-29, No. 5, in May 1982.

Finally, a U.S. Pat. No. 5,678,545, to Stratbucker from which the present invention was restricted is identified. Said 545 Patent teaches achieving electrical anisotropic properties in an adhesive sheet by entering one or more site(s) thereinto between electrodes.

Even in view of the above cited literature, need remains for a convenient to utilize bioelectric interface which comprises an electrically anisotropic hydropolymer self adhesive material, and further comprises equivalent Einthoven triangle limb electrodes on a common subject chest mounted support sheet, which biolelectrical interface allows accurately monitored signals to be obtained therefrom during use, and facilities, for instacne, practice of external cardiac pacing, external cardiac defibrillation, external electrosurgery and electro-ablation processes, and practice of impedance cardiography.

DISCLOSURE OF THE INVENTION

The present invention concerns the practice of electrocardiography wherein a number of electrical signals, which are diagnostic of myocardial function, are acquired via electrodes placed upon a subject's body. As regards this use, subject contacting electrodes can be spatially oriented in lead configurations such as Einthoven triangle, Frank, McFee, Schmidt, twelve-lead configurations etc., and in array patterns for use in mapping, etc. The present invention bioelectric interface can comprise a system which provides Right-Arm (RA), Left-Arm (LA) and Left-Leg (LL) electrodes which form, when applied to a subject's chest in use, an Einthoven frontal lead triangle with a I, II, III lead pattern, said pattern being determined as acceptable by presentation of a voltage with respect to ground at a formed Wilson common terminal (WCT), which voltage with respect to ground is within a selected range of deviation from a voltage with respect to ground which would present at a conventionally formed Wilson common terminal using conventional subject limb positioning of RA, LA and LL electrodes. A preferred present invention bioelectric interface further provides all necessary electrodes, appropriately configured for mounting to a subject's chest, for use with electrocardiograph systems.

As demonstrated in the Background Section of this Disclosure, multiple electrode systems are not unknown. However, said known systems do not provide all electrodes for use with a twelve-lead electrocardiogram (ECG) system conveniently positioned on a bioelectric interface which can be easily, accurately and repeatably applied to a subject's chest in a desired anatomical orientation. A twelve-lead (ECG) system, by conventional practice, requires that electrodes be placed on a subject's Right (RA) and Left (LA) arms and Left leg (LL), and that six precordial electrodes, (V1, V2, V3, V4, V5, and V6), be placed upon the subject's chest. The locations of the V1–V6 electrodes are:

V1—in the region of the fourth intercostal space at the right sternal border;

V2—in the region of fourth intercostal space at the left sternal border;

V4—in the region of fifth intercostal space at the left mid-clavicular line;

V3—in the region of the midpoint between the V2 and V4 electrodes;

V5—in the region of the fifth intercostal space at the left anterior axillary line;

V6—in the region of the fifth intercostal space in the left mid-axillary line.

No known reference, however, suggests that arm and leg electrodes should be placed at chest locations relatively near the precordial electrodes. The present invention teaches that said arm and leg electrodes are to be so placed. The location of said arm and leg electrodes is best understood by reference to the Drawings which are discussed in the Detailed Description of this Disclosure, however, verbally their positioning can be generally described as:

Right Arm—generally in the region of the second intercostal space to the right of the sternum;

Left Arm—generally in the region of left fourth intercostal space at the mid-axillary line; and Left Leg—generally in the region of the inferior costal margin within the left and right mid-clavicular lines, but preferably at the left mid-clavicular line.

In addition, the present invention teaches the optional use of multiple electrode element electrodes, (eg. "Bulls-eye" shaped electrodes), for instance, in a multiple electrode element electrode system. Use of single electrode element "Button" electrodes is conventional, and in use each such Button electrode serves to measure an electrical signal between it and a common or reference electrode, (typically termed uni-polar electrodes), or a similar button electrode (typically termed Bi-polar electrodes). When multiple electrode element (eg. Bulls-eye), electrodes are utilized, however, signals are generated between two components of a single electrode. Continuing, a Bulls-eye shaped electrode is typically configured like a "target". That is, typically a Button electrode will be centrally located within an outer annular shaped electrode. The benefits provided by such multi-electrode element electrodes are the ability to achieve greater resolution of signals generated in a specific area of a subject's heart, and it is noted, that the signals measured are representative of the derivatives of electrical signal activity produced by a subject's heart. That is, the signal provided between a Button and First Annulus is proportional to a derivative of a signal generated by a subject's heart. Additional annular ring electrodes can also be present and signals measured thereby are proportional to higher order derivatives. Use of Bulls-eye" electrode geometry then allows investigation of High Frequency aspects of electrical activity generated by a subject's heart. It is noted that a limitation is associated with the use of Bulls-eye electrodes in that the smaller they are dimensioned, although enabling increased resolution and investigation of electrical signals generated in smaller regions in a heart, the smaller the magnitude of signal they provide. In a multiple electrode setting then, where relative motion between electrodes can create confounding electrical noise, it then becomes increasingly important to prevent relative motion between electrodes and components of Bulls-eye electrodes, when Bulls-eye electrodes are present. (Note, it is emphasized that it is possible to achieve a result similar to that provided by "Bulls-eye" electrodes with other multiple element electrodes, and for the purpose of this Disclosure any functionally similar electrode is to be considered as included by the terminology "Bulls-eye" whether a closed annulus is present or not).

It is also to be understood that a present invention electrode can consist of a plurality of electrode elements, (eg. a plurality of button shaped electrode elements), configured in a region of the bioelectric interface which, in use, aligns with an anatomical location appropriate for use in a twelve-lead (ECG) system.

With the forgoing in mind, it is then to be appreciated that the system of the present invention is a bioelectric interface comprised of a plurality of electrodes which are affixed to a support sheet in a desired spatially separated pattern, such that in use said electrodes are essentially fixed in location with respect to one another. It is noted that fixing said relative position between electrodes, and between electrode elements, serves to reduce electrical noise which can be generated when, in use, electrodes move with respect to one another. Again, it is to be understood that the electrodes can be of single electrode element, or multiple electrode element Button or Bulls-eye, (or other), geometry.

Continuing, a typical present invention bioelectic interface has an adhesive material present over at least a portion of a surface thereof which contacts a subject in use. The adhesive material of the present invention can have the properties of simultaneously demonstrating essentially electrically anisotropicity, but isotropic mechanical (eg. pliability and adhesion), properties. That is, the specific impedance across the adhesive material can be significantly different from that laterally directed, but the mechanical properties such as adhesion and pliability are typically essentially consistent. (Note, the term "specific impedance" is used to refer to the regional bulk property of the adhesive material, rather than properties resulting from dimensions of sheets fabricated therefrom). In the preferred embodiment, the adhesive material is a hydropolymer sheet which demonstrates a tackiness on a subject skin contact side thereof. Hydropolymers are particularly applicable in realization of the present invention as they are electrically conductive, relatively nonirritating to a subject's skin, and they demonstrate excellent adhesive qualities. Commercially available hydropolymer sheets with isotropic electrical properties, are available from Promeon of Boston, Mass. under the product designation RG-60 Series Hydrogels. Lec-Tec of Minneapolis, Minn. also markets hydrogels. The present invention provides that such adhesive hydropolymer sheet material can be utilized, if "slits" are entered thereto at appropriate locations to effect electrical anisotropicity between electrodes present at various laterally offset locations. It is noted that hydropolymer sheets do not typically demonstrate a rigidity sufficient to maintain a spatially stable relationship between electrodes affixed thereto, but particularly when slits are formed therein, hence, the present invention requires that a support sheet carrier matrix be present to which electrodes and said adhesive sheet attach. That is, the system of the present invention will then comprise a support sheet carrier matrix to which are attached, at desired spatially offset locations, electrodes, over which configuration said hydropolymer is placed so that said electrodes are sandwiched between said carrier matrix and hydropolymer. At locations between the various electrodes said "slits" are then caused to be present by, typically, a mechanical process. It is noted that in practice said slits need not be of a degree to provide complete discontinuity between various regions of the resulting hydropolymer system to provide a sufficiently anisotropic specific impedance system. The Background Section also identifies various electrically anisotropic adhesive materials. The present invention, in addition, teaches that an essentially electrically anisotropic adhesive material sheet can be provided by a "Scrim" material comprising a number of channels therethrough, which channels are caused to be filled with an electrically conductive adhesive material, (preferably a hydropolymer), such that "island channels" of conductive material exist across the resultant sheet, but such that electrically nonconductive scrim exists between laterally oriented islands of conductive material. The "Scrim" can be electrically conductive carbon fibers, and/or electrically non-conducting plastic filaments, as required to provide a desired electrical anisotropicity.

Continuing, the present invention, in its preferred embodiment, teaches that while a family of bioelectric interface sizes is possible, one size of multiple electrode bioelectrical interface can be made sufficient for use with many subjects within a reasonable body size variation range. The present invention teaches that to accomplish placement of electrodes, such as defined infra for twelve-lead systems, on subject's bodies of various size, that groups of electrode elements should be available in the region of for instance, the fourth intercostal space at the right sternal border, (ie. the location for a V1 lead). In use then, regardless of a subject body size, one electrode element in a group of electrode elements in the region of the fourth intercostal space at the right sternal border, will provide an optimum result. Which electrode element in a group of electrode elements provides said optimum result, will of course be subject specific. Prior art has failed to recognize the need to provide a group of electrode elements in the region of a specific electrode placement location so that a user can select, manually or automatically, an appropriately placed electrode element for a specific subject.

It is also noted that as the relative spatial separation of various electrodes is essentially fixed by the present invention, and as their position on a subject's body is typically secured by an adhesive sheet, it is possible to conduct activities such as cardio-pulmonary-resuscitation (CPR) on a subject to which the present invention bioelectric interface is applied, without removal thereof. Such is essentially impossible where individual leads are utilized in an (ECG) system. As well, the present invention teaches that the means for making electrical contact to the electrodes should be available on the outer, non-subject contact, surface of the bioelectrical interface. For instance, snaps might be provided so that leads from any (ECG) system can easily attach thereto, or so that conductive tracks can be employed to bring signals to a manifold or connector means for convenient electrical access.

It is also emphasized that the electrodes in the bioelectric interface, being electrically conductive, enable, in an emergency, the application of defibrillation paddle-type electrodes to said interface means for making intimate electrical contact to said electrodes without removing the present invention bioelectrical interface from the subject. And, because the present invention is firmly affixed to a subject, the defibrillation shock will be safely transmitted to the subject with little, or no attenuation. It is also emphasized that in use, first and second conventional paddles of a defibrillation system can be caused to contact first and second spatially separated groups of electrodes in the bioelectric interface, press contacted electrodes into good electrical contact with the subject, and deliver electrical defibrillating pulse energy therethrough. Further, the presence of multiple electrodes, (and even multiple electrode elements within an electrode), within a defibrillation paddle-sized cluster of electrodes, through which defibrillation electrical energy can be delivered to a subject, serve to reduce adverse edge effects associated with applying defibrillation electrical energy through single element paddle, (or pad), electrodes. Special electrodes can be specifically designated which serve to reduce edge effects, and use thereof in the present invention Bio-electric interface is within the scope of the present invention.

One can also utilize one or more electrodes in the present invention bioelectric interface for heart pacing, electrosurgery, electro ablation and impedance cardiography.

The present invention bioelectric interface can be better described, in its most basic form, as comprising a support sheet in functional combination with at least three (3) spatially separated electrocardiogram system electrodes, with each of said at least three (3) spatially separated electrocardiogram system electrodes being a single electrical electrode element or a group of electrically independent electrode elements. Each of said spatially separated electrocardiogram system electrodes is affixed to said support sheet in a manner such that the relative positions of said electrocardiogram system electrodes with respect to one another are essentially fixed therewithin. Three (3) of said at least three (3) electrocardiogram system electrodes being configured in an RA, LA, LL electrocardiogram system electrode pattern. The positioning of said three (3) electrocardiogram system electrodes as applied to a subject's chest during use can be described as follows:

electrode RA being generally in the region of the second intercostal space to the right of the sternum;

electrode LA being generally in the region of the left fourth intercostal space in the mid-axillary line;

electrode LL being generally in the region of the inferior costal margin within the left and right mid-clavicular lines.

Further, said electrodes RA, LA and LL form, when applied to a subject's body in use, an Einthoven frontal lead triangle with a I, II, III lead pattern which is determined as acceptable by presentation of a voltage with respect to ground at a formed Wilson common terminal (WCT), which voltage with respect to ground is within a selected range of deviation from a voltage with respect to ground presented at a conventionally formed Wilson common terminal using conventional subject limb positioning of RA, LA and LL electrodes. Said user selected range of voltage deviation can be selected to be less than one (1.0) millivolt, one (1.0) millivolt, or greater than one (1.0) millivolt, such that familiar precordial lead (ECG) tracings are achievable. It is specifically noted that (ECG) signals from I, II and III leads will typically be somewhat different that (ECG) signals from I, II and III leads formed from subject limb positioned electrodes.

The present invention bioelectric interface can further comprise an electrocardiogram system RL electrode, and any or all of said RA, LA, LL and RL electrode(s) can be present in the support sheet such that perforations allow easy detachment of said electrocardiogram RA, LA, LL and RL electrodes, in use, thereby allowing them to be easily positioned at a location in contact with a subject's chest, or by manual manipulation, in conventional subject limb positions.

The present invention bioelectric interface support sheet is typically at least partially covered with an adhesive material on a subject contacting side thereof, and said adhesive material can present with electrical conductive properties which can be isotropic, or regionally anisotropic such that the specific impedance through said adhesive material is less than in a laterally oriented direction. Said regional anisotropic electrical conductive properties of said adhesive material can be effected, as described infra herein, by the presence of an electrically conductive and/or non-conductive scrim patterned therein so as to form channel regions of electrically conductive adhesive material through said adhesive material bordered by said scrim material, such that adhesive material in one channel region does not contact that in other regions. An alternative approach to effecting said regional anisotropic electrical conductive properties of the adhesive material involves the placing of slits therein. Said adhesive material can be a hydropolymer and it can be caused to cover essentially the entire subject contacting surface of said support sheet.

It is emphasized that the present invention bioelectric interface comprises an adhesive sheet in functional combination with at least two spacially separated electrodes, wherein the adhesive sheet simultaneously presents with essentially anisotropic specific impedance properties and essentially isotropic mechanical pliability and adhesion properties and the electrodes are affixed to the adhesive in a manner such that their relative positions with respect to one another are essentially fixed. The specific impedance from each said electrode directly through said adhesive sheet, is less than that between any said electrodes through said adhesive sheet, preferably as a result of there being scrim therein, which scrim is a web of electrically relatively non-conductive material with relatively electrically conductive adhesive material present in open areas of said web so as to form channel regions of electrically conductive adhesive material bordered by said scrim material, such that adhesive material in one channel region does not contact that in other regions.

As mentioned, at least one of said spatially separated electrocardiogram system electrodes can be of a construction consisting of a group of electrically independent electrode elements, and said elements can be configured in, for instance, Bulls-eye and multiple button shaped electrode elements patterns.

A method of providing an Einthoven triangle, RA, LA, LL pattern of electrodes on the chest of a subject, utilizing the present invention bioelectric interface, can comprise the steps of:

a. Providing a present invention bioelectric interface comprising a support sheet in functional combination with at least three (3) spatially separated electrocardiogram system electrodes as already described, wherein at least one (1) of said at least three (3) spatially separated electrocardiogram system electrodes is of a construction consisting of a group of electrically independent electrode elements. As described above, each of said spatially separated electrocardiogram system electrodes is affixed to said support sheet in a manner such the relative positions of said electrocardiogram system electrodes with respect to one another are essentially fixed therewithin. Three (3) of said at least three (3) electrocardiogram system electrodes are configured in an RA, LA, LL electrocardiogram system electrode pattern, such that said three (3) electrocardiogram system electrodes are applied on a subject's chest during use as follows:

electrode RA being generally in the region of the second intercostal space to the right of the sternum;

electrode LA being generally in the region of the left fourth intercostal space in the mid-axillary line;

electrode LL being generally in the region of the inferior costal margin within the left and right mid-clavicular lines;

b. Applying said bioelectric interface to a subject;

c. Selecting at least one electrically independent element in each of said at least one electrocardiogram system RA, LA and LL electrode(s) consisting of a group of electrically independent electrode elements;

d. Connecting said selected electrocardiogram system electrically independent element(s) in each of said RA, LA and LL electrode(s) to appropriate inputs of an electrocardiogram system.

(Note, as described above, said electrode RA, LA and LL form, when applied to a subject's body in use, an Einthoven frontal lead triangle with an I, II, III lead pattern which is determined as acceptable by presentation of a voltage with respect to ground at a formed Wilson common terminal (WCT), which voltage with respect to ground is within a selected range of deviation from a voltage with respect to ground presented at a conventionally formed Wilson common terminal using conventional subject limb positioning of RA, LA and LL electrodes. Said user selected range of voltage deviation can be selected to be less than one (1.0) millivolt, one (1.0) millivolt, or greater than one (1.0) millivolt with the criteria being that acquisition of familiar Precordial lead (ECG) tracings are enabled).

Continuing, a preferred embodiment of the present invention bioelectric interface comprises a support sheet in functional combination with at least nine (9) spatially separated electrocardiogram system electrodes. Each of said at least nine (9) spatially separated electrocardiogram system electrodes being a single electrical electrode element or a group of electrically independent electrode elements. Each of said spatially separated electrocardiogram system electrodes is affixed to said support sheet in a manner such the relative positions of said electrocardiogram system electrodes with respect to one another are essentially fixed therewithin, with nine (9) of said at least nine (9) electrocardiogram system electrodes being configured in an RA, LA, LL, V1, V2, V3, V4, V5, V6 electrocardiogram system electrode pattern. In use, said nine (9) electrocardiogram system electrodes are applied to a subject's chest during use as follows:

electrode RA being generally in the region of the second intercostal space to the right of the sternum;

electrode LA being generally in the region of the left fourth intercostal space in the mid-axillary line;

electrode LL being generally in the region of the inferior costal margin within the right and left mid-clavicular lines.

Again, said electrodes RA, LA and LL form, as described infra herein, when applied to a subject's body in use, as Einthoven frontal lead triangle with an I, II, III lead pattern which is determined as acceptable by presentation of a voltage with respect to ground at a formed Wilson common terminal (WCT), which voltage with respect to ground is within a selected range of deviation from a voltage with respect to ground which would be provided by a conventionally formed Wilson common terminal (WCT) using conventional subject limb positioning of RA, LA and LL electrodes. Said user selected range of voltage deviation can be selected to be less than one (1.0) millivolt, one (1.0) millivolt, or greater than one (1.0) millivolt.

The V1, V2, V3, V4, V5, V6 electrocardiogram system precordial electrode pattern is formed as:

electrode V1 in the region of the fourth intercostal space at the right sternal border;

electrode V2 in the region of the fourth intercostal space at the left sternal border;

electrode V4 in the region of the fifth intercostal space at the left mid-clavicular line;

electrode V3 in the region of the midpoint between electrodes V2 and V4;

electrode V5 in the region of the fifth intercostal space in the left anterior axillary line; and electrode V6 in the region of the fifth intercostal space in the left mid-axillary line.

The described preferred embodiment of the present invention can also further comprise an electrocardiogram system RL electrode, and perforations can be present in said support sheet to allow easy detachment and deployment of said electrocardiogram RA, LA, LL and RL electrodes, in use, so that they can be positioned in contact with a subject's chest, or in conventional subject limb position.

As described above, the presently described present invention bioelectric interface support sheet is also typically at least partially covered with an adhesive material on a subject contacting side thereof, which adhesive material present with electrical conductive properties which can be isotropic or regionally anisotropic such that the specific impedance through said adhesive material is less than that in a laterally oriented direction. As also already discussed, a preferred adhesive material is hydropolymer which covers essentially the entire subject contacting surface of said support sheet.

Also as discussed above, each of the electrodes can be of a construction consisting of a group of electrically independent electrode elements, such as a Bulls-eye pattern, and multiple button shaped electrode elements.

A present invention bioelectric Interface can also comprise electrodes with spring-loaded means on the non-subject contacting side of at least one of said electrodes, which spring-loaded means develop compression derived force when caused to be compressed. The purpose thereof is to facilitate electrical contact to an electrically conductive means, (such as a defibrillation paddle), caused to be placed in contact therewith by compression derived force. This is particularly effective where at least two electrodes have spring loaded means present such that when said electrically conductive element is placed in contact with said at least two spring loaded means, both are caused to be in good electrical contact therewith by compression derived force, and is best utilized where utilized in a plurality of electrodes for mounting to a subject's chest as in claim 2 in which the electrodes are positioned for use in 12 lead ECG monitoring on a subject's chest.

Continuing, a method of acquiring electrocardiographic data can comprise the steps of:

a. Providing a bioelectric interface comprising a support sheet in functional combination with at least nine (9) spatially separated electrocardiogram system electrodes, as just described;

b. Affixing said bioelectric interface to a subject's chest as described above, and causing electrodes therein to be electrically attached to an electrocardiographic system such that familiar electrocardiographic data is obtained. It is noted that acquiring familiar precordial (ECG) data requires development of a voltage at a Wilson central terminal (WCT) formed by "Y" interconnecting resistors or impedances from the RA, LA and LL electrodes which is within some selected range of deviation from a voltage developed by at a Wilson central terminal (WCT) formed by "Y" interconnecting resistors or impedances from electrodes conventionally affixed to a subject's limbs. This is because signals from percordial electrodes are referenced to the Wilson central terminal (WCT).

Said method of acquiring electrocardiographic data said method of acquiring electrocardiographic data can further include the step of providing a present invention bioelectric interface that has perforations which allow easy detachment and deployment of limb leads, and removing and deploying said electrodes RA, LA and LL configured in an Einthoven frontal triangle LA, RA, LL pattern, utilizing said perforations in said support sheet, and deploying and affixing said RA, LA and LL electrodes to conventional subject limb locations.

A method of utilizing any present invention bioelectric interface during formation of a present invention Einthoven triangle or during acquisition of electrocardiographic data, can further comprise the simultaneous step of performing a procedure selected from the group consisting of;

a. cardio-pulmonary resuscitation
b. cardiac defibrillation;
c. cardiac pacing;
d. electro surgery;
e. electro-ablation; and
f. impedance cardiography.

on said subject without removing said bioelectric interface.

Where defibrillation is performed, two conventional defibrillation paddles can be positioned so that a first conventional defibrillation paddle contacts at least two of said electrocardiogram system electrodes, and a second said conventional defibrillation paddles contacts at least two of said electrocardiogram system electrodes, said two at least electrodes contacted by said first conventional defibrillation paddle being different than, and spatially separated from, said at least two electrodes contacted by said second conventional defibrillation paddle. In use, electrodes contacted by defibrillation paddles are caused to be pressed firmly into good contact with a subject. The result of the presence of multiple electrodes being that defibrillation pulse current distribution electrode edge effects are reduced. Alternatively, defibrilation impulses can be provided between two groupings of pluralities of electrodes, (electrodes in a plurality thereof being paralleled), in a present invention bioelectric interface via wires or equivalent electrical conductor means.

It is further noted that the voltage present at a formed Wilson common terminal can be a root-mean-square value of a selected portion of a subject electrocardiogram system monitored electrocardiogram cycle, such as the QRS complex.

It is noted that a conventional Wilson common terminal is a central "Y" interconnection point of fixed value, (eg. 10,000 ohm), resistors or impedances attached to RA, LA and LL electrodes. The present invention provides that at least one of said resistors can be variable and can, in use, be adjusted and thereby set a Wilson common terminal voltage produced by use of a present invention Bioelectric Interface, to a desired value. The application of variable resistors in forming a Wilson common terminal in combination with a present invention Bioelectric Interface, to effect production of a Wilson common terminal voltage which is within a desired deviation value with respect to a similar voltage which would be obtained utilizing conventional limp positioned electrodes, is not, to the inventor's knowledge, obviated in any known reference or combination of references.

It is further noted that the "ground" referred to when describing the Wison common terminal (WCT) voltage with respect to ground, can be taken to be the Left leg (LL) electrode.

Finally, it is to be understood that a present invention bioelectric interface can be generally described as comprising at least one selection from the group consisting of:

a. an adhesive sheet which simultaneously presents with essentially anisotropic impedance properties and essentially isotropic mechanical pliability and adhesion properties, said electrode being affixed to said adhesive sheet in a manner such that their relative positions with respect to one another are essentially fixed, and such that the impedance from each said electrode directly through said adhesive sheet, is less than that between any said electrodes through said adhesive sheet;

b. perforations in said support sheet which allow easy detachment and deployment of at least one of said Einthoven frontal lead triangle enabling RA, LA and LL electrodes, so that said at least one of said Einthoven triangle RA, LA, and LL electrodes is/are, in use, postionable at locations selected from the group consisting of:

in contact with a subject's chest; and
  in conventional Einthoven triangle forming subject limb positions;

c. an undulated outer edge on said bioelectric interface support sheet; and d. at least one hole through said bioelectric interface support sheet which allows access to the skin of a subject to which it is affixed in use, (eg. over the xiphiod process of a subject to which said bioelectric interface is applied in use).

Said group might also include the presence of cocklebur-like means at electrode-subject contact positions, to improve subject contact.

The present invention will be better understood by reference to the Detailed Description Section in conjunction with the accompanying Drawings.

SUMMARY OF THE INVENTION

It is a primary purpose of the present invention to teach a bioelectric interface which includes an adhesive sheet in functional combination with at least two spacially separated electrodes. The adhesive sheet simultaneously presents with essentially anisotropic specific impedance properties and essentially isotropic mechanical pliability and adhesion properties and the electrodes are affixed to the adhesive sheet in a manner such that their relative positions with respect to one another are essentially fixed. The specific impedance from each said electrode directly through said adhesive sheet, is less than that between any said electrodes through said adhesive sheet, as a result of there being slits or scrim therein, which scrim is a web of electrically relatively non-conductive material with relatively electrically conductive adhesive material present in open areas of said web so as to form channel regions of electrically conductive adhesive material bordered by said scrim material, such that adhesive material in one channel region does not contact that in other regions.

It is a another primary purpose of the present invention to teach that electrodes secured in a support sheet and configured in an RA, LA, LL electrocardiogram system electrode pattern in a bio-electric interface should be applied to a subject's chest during use, the positioning of said electrocardiogram system electrodes being, for instance:

electrode RA being generally in the region of the second intercostal space to the right of the sternum;

electrode LA being generally in the region of the left fourth intercostal space at the mid-axillary line;

electrode LL being generally in the region of the inferior costal margin, preferably in the left mid-clavicular line;

said electrodes RA, LA and LL forming an Einthoven frontal lead triangle with a I, II, III lead pattern which is determined as acceptable by presentation of a voltage with respect to ground at a formed Wilson common terminal, which voltage with respect to ground is within a selected range of deviation from a voltage with respect to ground presented at a conventionally formed Wilson common terminal using conventional subject limb positioning of RA, LA and LL electrodes. (Said user selected range of voltage deviation can be selected to be less than one (1.0) millivolt, one (1.0) millivolt, or greater than one (1.0) millivolt).

It is another purpose of the present invention to teach that six precordial electrodes (V1, V2, V3, V4, V5, and V6) in said bioelectric interface, should also be placed upon the subject's chest in combination with said RA, LA and LL electrodes. The locations of the V1–V6 electrodes being:

V1—in the region of the fourth intercostal space at the right sternal border;

V2—in the region of fourth intercostal space at the left sternal border;

V4—in the region of fifth intercostal space at the left mid-clavicular line;

V3—in the region of the midpoint between the V2 and V4 electrodes;

V5—in the region of the fifth intercostal space at the left anterior axillary line;

V6—in the region of the fifth intercostal space in the left mid-axillary line.

It is yet another purpose of the present invention to teach the use of multiple electrode element electrodes, (eg. "Bullseye" shaped electrodes), as well as single electrode element "Button" electrodes in a bioelectric interface.

It is still yet another purpose of the present invention to teach a bioelectric interface which has an adhesive material present over at least a portion thereof on a surface which contacts a subject in use.

It is yet still another purpose of the present invention to teach a bioelectric interface in which the adhesive material is a hydropolymer.

It is another purpose of the present invention to teach a bioelectric interface in which the adhesive material demonstrates anisotropic specific impedance.

It is yet another purpose of the present invention to teach a method of utilizing any present invention bioelectric interface during formation of an Einthoven triangle equivalent or during acquisition of electrocardiographic data, which further comprises the simultaneous step of performing a procedure selected from the group consisting of;
a. cardio-pulmonary resuscitation
b. cardiac defibrillation;
c. cardiac pacing;
d. electro surgery;
e. electro-ablation; and
f. impedance cardiography.
on said subject without removing said bioelectric interface.

It is still yet another purpose of the present invention to teach a bioelectric interface comprised of a plurality of electrodes which are affixed to a support sheet in a desired spatially separated pattern, such that in use said electrodes are essentially fixed in location with respect to one another such that confounding noise signals resulting from relative motion between said electrodes are reduced in use.

It is another purpose of the present invention to describe the use of variable resistor(s) in formation of a Wilson common terminal. The purpose thereof being to allow adjustment of a voltage appearing at a Wilson common terminal formed utilizing present invention Bioelectric Interface RA, LA and LL electrodes, so that it is within a desired range of deviation from a Wilson common terminal voltage obtained utilizing conventionally placed limb electrodes.

It is another general purpose yet of the present invention to teach that a bioelectric interface should be characterized by a support sheet which comprises at least one, or two selection(s) from the group consisting of the presence of:

electrically anisotropic adhesive covering a subject contacting side thereof;

an undulated outer edge;

holes therethrough which allow access to a subject's skin in use;

perforations therein which allow easy detaching and deployment of electrodes therefrom; and at least one electrocardiogram electrode(s) with spring-loaded means on a non-subject contacting side thereof to facilitate electrical contact to an electrical element caused to be placed in contact therewith.

BRIEF DESCRIPTION OF THE DRAWINGS

FIG. 2 shows a view of a two electrode bioelectric interface with a common adhesive sheet applied thereto, in which common adhesive sheet is present an electrically anisotropic property causing slit present between.

FIGS. 9a and 9b show defibrillation paddle electrical contact enhancing spring-loaded piston type electrode contact means.

DETAILED DESCRIPTION

Figure 1A:
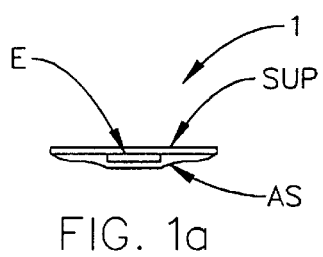
FIG. 1a shows a side elevational view of a bioelectric interface showing an electrode "sandwiched" by an adhesive sheet and a carrier matrix.
Figure 1B:
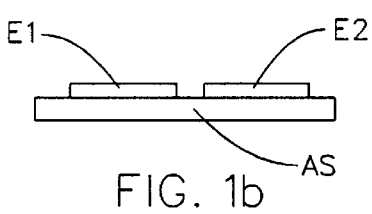
FIG. 1b shows a side elevational view of two electrodes situated on an adhesive sheet in essentially fixed relative positions with respect to one another.

Turning now to the Drawings, there is shown in FIG. 1a, a side elevational cross-sectional view of a single electrode (E) in a bioelectric interface (1) system comprising a Support Sheet (SUP) and an adhesive material (AS). Note that the electrode (E) is "sandwiched" between the Support Sheet (SUP) and adhesive material (AS). This is a typical arrangement, but where an adhesive material can provide sufficient spatial positioning integrity it is to be understood that the Support Sheet (SUP) can become unnecessary. FIG. 1b shows a side elevational view of two electrodes (E1) (E2) affixed to an adhesive sheet (AS) with a slit positioned therebetween.

Figure 2:
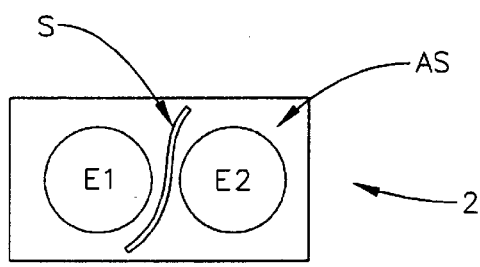

FIG. 2 shows a bioelectric interface system (2) comprised of two electrodes (E1) and (E2) looking from the surface thereof upon which is present an adhesive material (AS), (ie. that surface which will contact a subject's skin in practice). Note that a "slit" (S) is shown as present between said electrodes (E1) and (E2). In the case where the adhesive material is made of an electrically isotropic material, (eg. commercially available hydropolymers in sheet form for instance), it has been found that providing a slit (S) between two electrodes (E1) and (E2) effects essentially electrically anisotropic properties thereto. That is, a lower specific impedance will be measured from an electrode through the adhesive material than between two electrodes. In the case that an adhesive material provides such anisotropic electrical specific impedance properties, said slit (S) typically becomes unnecessary. It is noted that the reason the adhesive material should provide anisotropic electrical properties is that in an (ECG) setting, for instance, if the adhesive material is electrically isotropic, signals which should be present in one electrode in a bioelectric interface, will to some extent be present in other electrodes as well, as a result of lateral current flow through said adhesive material, and many prior multiple electrode systems therefore, enter an artifact to (ECG) data as a result. As well, adhesive material electrical anisotropy allows use of higher resolution electrode geometry, (discussed supra) because lateral current flow is limited.

It will be noted that the adhesive material (AS) in FIG. 2 is not completely bisected by the slit (S). This is a preferred, but not limiting practice, because complete electrode isolation is not always optimum. For instance, in (ECG) system settings it is common to inject a noise compensating signal to a Right Leg electrode via a driver circuit, which signal is to be imposed upon all electrodes. This practice is well known by practitioners in the (ECG) field, with noise compensating current flow normally being through a subject's skin, but is has been found that allowing some electrical path through the adhesive material does not noticeably degrade acquired (ECG) data. With that through in mind it is noted that a goal of the present invention is to provide a very firm affixation to a subject's body such that spatial separation between electrodes is maintained constant and such that good electrical contact between electrodes an a subject's skin is effected, via said adhesive material. Hence, the more surface area of the present invention bioelectric interface upon which the adhesive material remains present, the better.

Figure 3A:
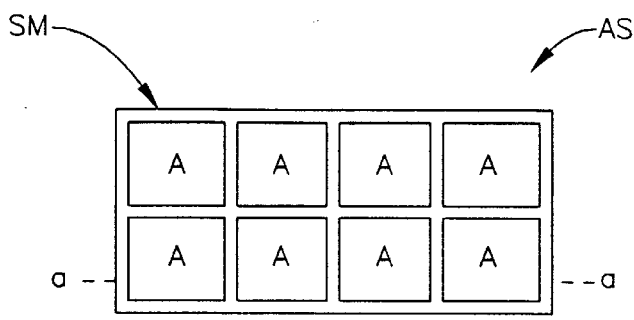
FIGS. 3a and 3b show top and side elevation views respectively of a novel electrically anisotropic adhesive sheet.

FIG. 3a shows a present invention system for providing electrically anisotropic specific impedance in an "adhesive sheet". Shown is an electrically non-conductive "Scrim" (SM) present in a form which provides numerous channel regions, said channel regions being filled with electrically isotropic conductive adhesive material (A).

Figure 4A:
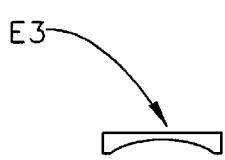
FIGS. 4a and 4b show various designs for electrodes.
Figure 4B:
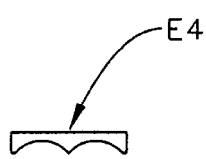
Figure 4C:
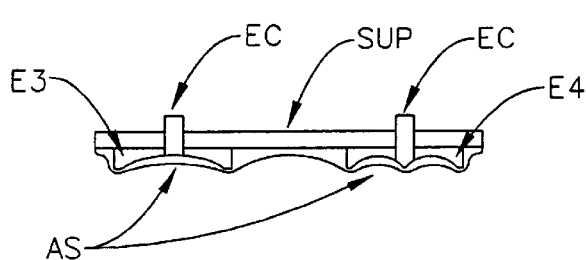
FIG. 4c shows the electrodes of FIGS. 4a and 4b between a carrier matrix and adhesive sheet including a cocklebur structure means.

Turning now to FIGS. 4a and 4b, there are shown preferred shapes (E3) and (E4) for electrodes. Note that there are regions of said electrodes which will ten to project into an adhesive material (AS) placed in contact therewith. The effect of said projection is to provide a thinning of the adhesive material (AS) and effect an electrically anisotropic character to the adhesive material (AS) as viewed in cross section. That is, electrical impedance from an electrode (E3) or (E4) through said adhesive material (AS) will be caused to be less than that between electrodes (E3) and (E4) through said adhesive material (AS), because of a thinning effect at the projecting edges of said electrodes. FIG. 4c demonstrates what can be described as a "cocklebur structure means" in an electrode wherein the projection (E4) serves to provide subject electrical contact improvment, perhaps even projecting through the adhesive material (AS). FIG. 4c also shows the presence of external device electrical connector means (EC).

Figure 5A:
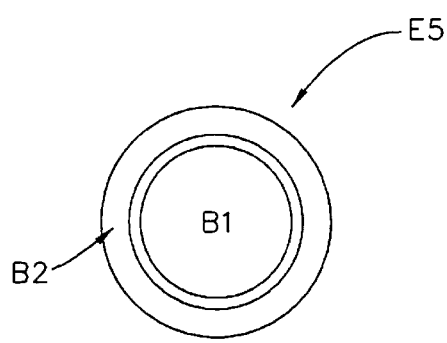
FIG. 5a shows a multi-element electrode configured in a Bulls-eye pattern.
Figure 5B:
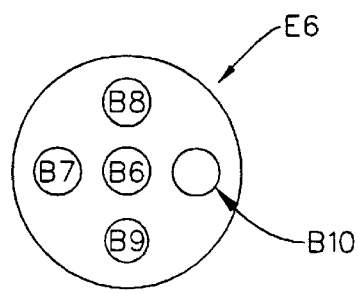
FIG. 5b shows a multi-element electrode pattern configured from button electrodes.

FIG. 5a shows an example of a multi-element electrode (E5) with a "Bulls-eye" geometry. As described in the Disclosure of the Invention Section of herein, use of said multiple element electrodes allows investigation of high frequency components in (ECG) signals, and allows better spatial resolution of the sources of monitored (ECG) signals. (It is to be understood that the "Bulls-eye" shape is an example of a multi-element electrode, and that any functionally similar multi-element electrode configuration is to be considered as included within the term "Bulls-eye"). The underlying distinction between multi-element electrodes and single element electrodes being that multiple single element electrodes typically utilize a single common electrode as a reference, whereas multi-element electrodes provide their own reference point. It will be appreciated that electrical anisotropicity can become very important in view of the higher resolution capability of "Bulls-eye" electrodes, when signals are being monitored from closely positioned points of, for instance a human heart muscle. That is, greater resolution capability is of no consequence if the signal reaching a sensing electrode is effected by lateral current flow through an attached adhesive material, which signal was originated by a distal source. FIG. 5b shows a plurality of "Button" electrode elements (B6), (B7), (B8), (B9) and (B10) which comprise an electrode (E6). Such an arrangement is beneficially utilized in a present invention Bioelectric Interface meant for use in Defibrillation. The well known "Edge" effect which results in uneven current distribution over the region of an electrode can be reduced by such a configuration.

Figure 6A:
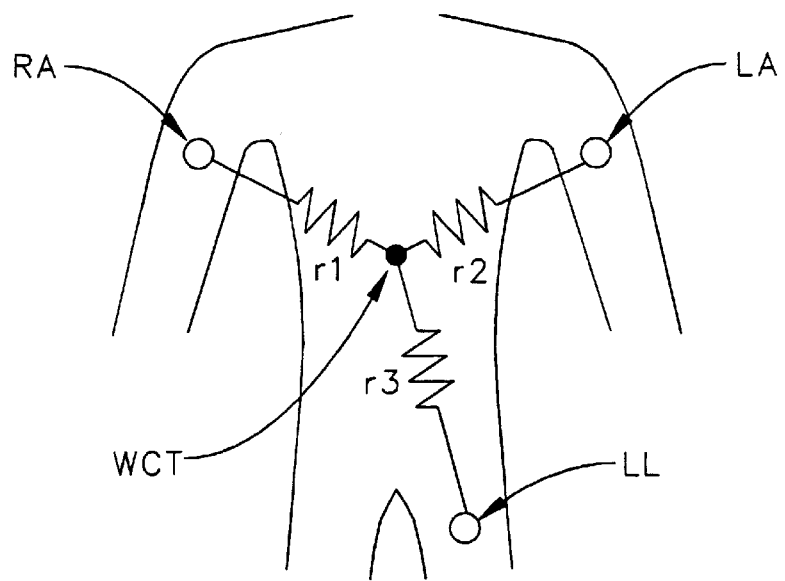
FIG. 6a shows a partial frontal view of a human torso, with formation of a Wilson Common Terminal from standard RA, LA and LL electrodes indicated.
Figure 6B:
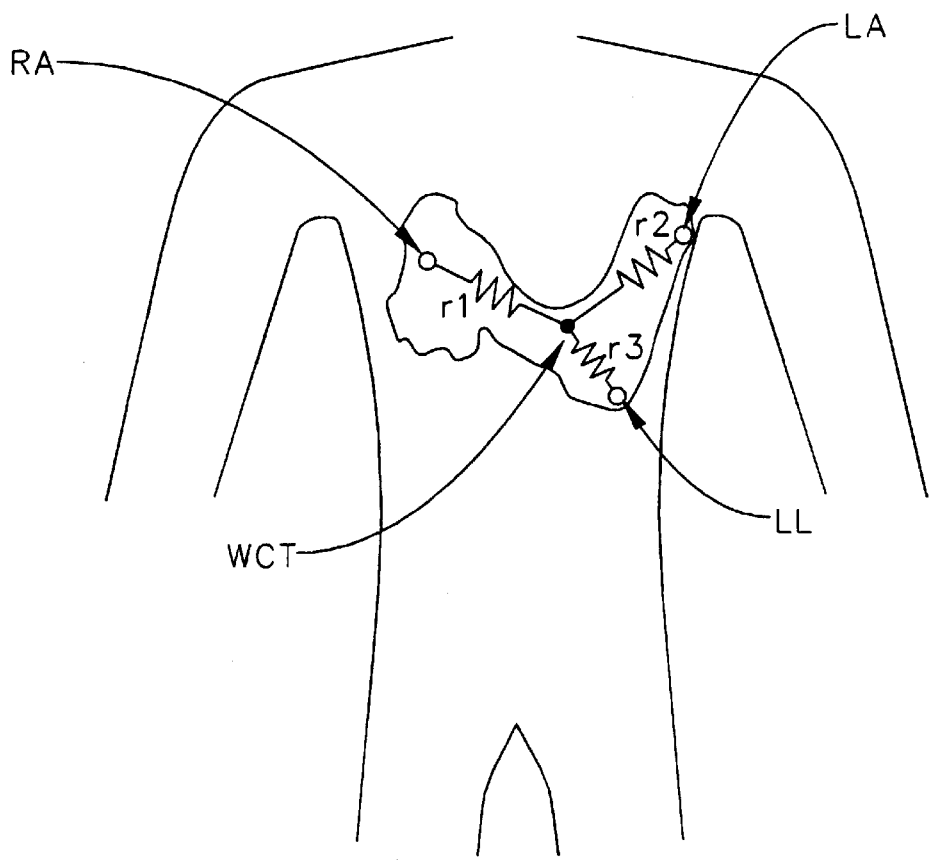
FIG. 6b shows a partial frontal view of a human torseau, with formation of a Wilson Common Terminal indicated, as formed from chest mounted RA, LA and LL electrodes of the present invention bioelectric interface.

FIG. 6a shows a partial human torso with RA, LA and LL electrodes placed on the limbs. Also shown is an Einthoven triangle Wilson Common Terminal (WCT) formed by attaching resistors to said RA, LA and LL electrodes, which resistors have a common central connection so as to form a "Y" circuit. FIG. 6b shows a partial human torso with RA, LA and LL electrodes placed on the chest as is effected by the present invention Bioelectric Interface (3). Also shown in an Einthoven frontal I, II, III lead triangle, Wilson Common Terminal (WCT) formed by attaching resistors (r1), (r2) and (r3) to said RA, LA and LL electrodes, which resistors have a common central connection so as to form a "Y" circuit. (Note, in use, the (WCT) voltage serves as a reference for precordial leads from V1, V2, V3, V4, V5 and V6 as are described elsewhere herein, for the FIGS. 6a and 6b cases, and equivalence thereof in both cases allows acquiring familiar precordial ECG data from both).

It is the result of the present invention that voltages which appear at Wilson Common Terminals shown in FIGS. 6a and 6b, each with respect to ground, are within some acceptable variance, (eg. 1.0 millivolt), therebetween, if the present invention RA, LA and LL electrodes are appropriately positioned within the FIG. 6b demonstrated bioelectric interface. A method of accomplishing this can be aided by causing at least one of the RA, LA and LL electrodes to be comprised of a plurality of electrically independent electrode elements, (as demonstrated in FIG. 7b). A user can, manually or via automation, optimally select an element in each RA, LA and LL electrode. As well, resistances (r1, r2 and/or r3), can be variable and a user can vary one or more of them.

Figure 7A:
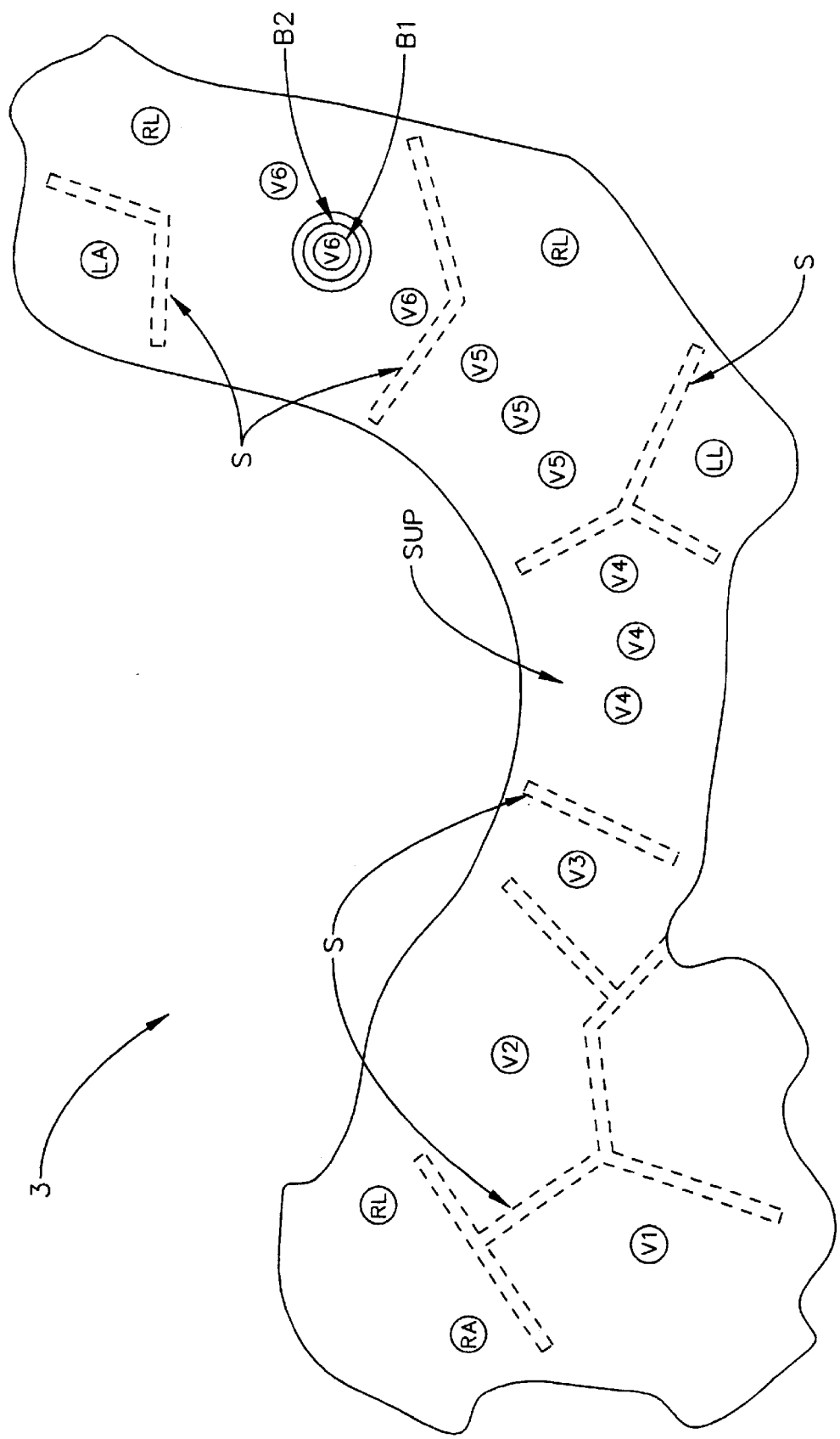
FIG. 7a shows a bioelectric interface configured for use with a twelve lead (ECG) system. Shows are groups of electrodes which serve to allow a "one-size to fit many" result. Also shown is an exemplary presence of a multi-element Bulls-eye electrode, and the presence of "slits" in an adhesive sheet to effect electrical anisotropic properties therein.

Turning now to FIG. 7a there is shown an approximately "actual size" typical present invention bioelectric interface system (3) with electrodes present therein and appropriately spatially distributed and positioned for use with a twelve lead (ECG) system. FIG. 7a shows the surface of the present invention bioelectric interface (3) opposite to that upon which is typically present an adhesive material which contacts a subject's skin in use. In use the bioelectric interface system (3) will typically be placed upon a subject's chest with the various precordial V1–V6 electrodes, and electrode groups, placed as follows:

electrode V1—in the region of the fourth intercostal space at the right sternal border.

electrode V2—in the region of the fourth intercostal space at the left sternal border;

electrode V4—in the region of the fifth intercostal space at the left mid-clavicular line;

electrode V3—in the region half way between electrodes V2 and V4;

electrode V5—in the region of the fifth intercostal space at the left anterior axillary line; and electrode V6—in the region of the fifth intercostal space at the left mid-axillary line.

Note that electrodes V4, V5 and V6 are each shown as a group of electrode elements. The present invention provides for any of the electrodes V1–V6 and any other electrodes which might be present, to be present as a group thereof. The reason for this is that the present invention bioelectric interface is, to some extent, a "single size fits many". That is, even though subject's body sizes vary greatly one to another, the present invention can be applied to essentially any non-deformed subject and an electrode within a group of electrodes in the region of an appropriate location will be found to be properly positioned for use, within an error which exists even if individual electrodes are utilized, (said error originating from improper application of a single electrode). It is emphasized that while only V4, V5 and V6 precordial electrodes are shown as groups of electrode elements in FIG. 7a, any electrode shown, or any other configuration of electrode elements utilized, can be present as a group of electrodes an necessary to effect the "one-size-fits-many" feature of the present invention bioelectric interface system. The reason that FIG. 7a shows electrodes V1, V2 and V6 as single electrodes and electrodes V4, V5 and V6 as shown as groups of electrode elements is that, in practice, application of the present invention bioelectric interface system to a subject's body will proceed in a manner that typically assures appropriate positioning of electrodes V1, V2 and V3 on a subject's chest. The remaining electrodes will then make contact with the subject's body at locations based upon the size and shape of the bioelectric interface (3), which for any specific electrode might or might not be at the generally accepted locations recited infra. Where a group of electrodes is present, however, it should be appreciated that one of the electrodes in the group will be found to be more appropriately positioned than the others of the group. It is also noted that where groups of electrodes are present, unused electrodes in a group can be utilized as, for instance, electrodes to effect cardiac pacing. As well, if one electrode in a group becomes inoperable, another can be substituted and still allow acquisition of reasonable (ECG) data. (See FIGS. 7b and 7c for other non-limiting examples). Also, multiple electrodes can be combined in a parallel configuration to allow greater current carrying capability during, for instance, defibrillation procedures.

Shown also in FIG. 7a are also the Right Arm (RA), Left Leg (LL) and Left Arm (LA) electrodes, positioned as appropriate for use as an Einthoven triangle configuration pattern, and for use as Right Arm (RA), Left Leg (LL) and Left Arm (LA) electrodes in the present invention bioelectric interface. Said electrodes are positioned are:

electrode (RA)—in the general region of the second intercostal space to the right of the sternam;

electrode (LA)—in the general region of the left fourth intercostal space at the mid-axillary line; and electrode (LL)—in the general region of the inferior costal margin between the right or left mid-clavicular lines.

(Note, multiple electrodes designated Right Leg (RL) are also present. As alluded to above, the Right Leg (RL) electrode in (ECG) settings is typically utilized to inject an out-of-phase noise compensating signal, which can be functionally applied to many electrodes. It has been determined that said noise compensating signal can be injected at any essentially any location on the present invention bioelectric interface without degradation of the results).

Figure 3B:
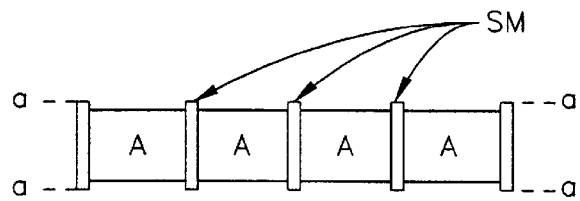

Also note that slits (S) in an electrically isotropic adhesive material are shown in broken lines. As viewed, said adhesive material would be present on a lower surface of the shown present invention bioelectric interface (3), hence are shown as viewed through the adhesive material and indicated Support Sheet (SUP). Said slits (S) will be less necessary, and probably unnecessary, where an adhesive material constructed from an inherently electrically anisotropic material, such as demonstrated by FIGS. 3a and 3b, is utilized. In such systems the scrim (SM) can provide structural integrity, while the present electrically conductive adhesive can provide sufficient adhesive contact and electrical conductivity.

Also note that FIG. 7a shows one of the V6 electrodes as a "Bulls-eye" electrode with a central Button (B1) and outer annular ring (B2) present. Again, this is demonstrative, and in effect all electrodes could be of a multi-element construction. The conductive polymer will typically, though not necessarily, be discontinuous between the element of a multi-element electrode. Note than the central Button (B1) can still serve as a standard Button electrode. In use, one could also interconnect the V6 (B1) and (B2) elements, or all the electrodes in a group, (for instance, if it became necessary to defibrillate a subject while a present invention bioelectric interface is in place). Conventional practice would require removal of any such electrode providing system. However, where the present invention bioelectric interface (3) is present, a defibrillation paddle could be positioned to effectively form a single electrode from electrodes in the V4, V5 and V6 groups. (Note said defibrillation paddle could contact external contact means (EC) such as shown in FIG. 4c). A second defibrillation paddle could likewise be simultaneously applied to the V1, V2 and V3 electrodes, or group of electrodes should alternatives be present at V1, V2 and V3 electrode locations. (See FIG. 7d for indication of Defibrillation Paddles in use).

Again, FIG. 7a provides a non-limiting example of a Bioelectric Interface (3) of the present invention. The present invention is, however, in the combination of the various disclosed elements thereof, in their various forms, as well as in electrode positioning.

Figure 7B:
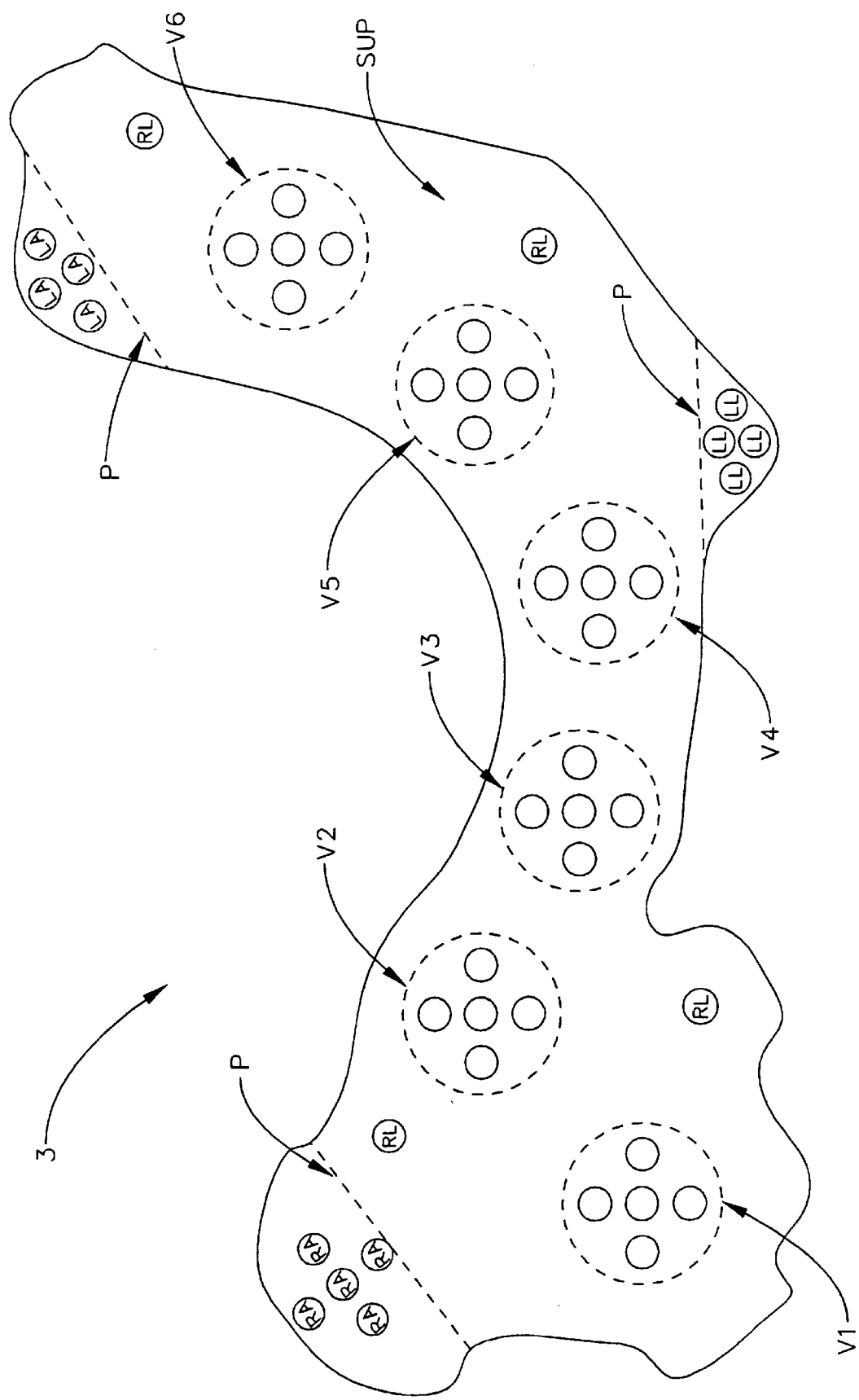
FIG. 7b shows a bioelectric interface configured for use with a twelve lead (ECG) system. Shown are groups of electrodes made of a plurality of electrode elements as shown in FIG. 5b. Shown also are perforations in a continuous support sheet for use in detaching leads used in forming an Einthoven triangle Left Arm, Right Arm and Left Leg pattern.

Continuing, FIG. 7b shows a present invention Bioelectric Interface (3) with electrodes consisting of a FIG. 5b electrode element arrangement present at all V1, V2, V3, V4, V5 and V6 locations in the Support Sheet (SUP). RA, LA and LL electrodes are also shown to comprise multiple electrode elements. As in FIG. 7a, the Bioelectric Interface is viewed from the non-subject contacting side, and indications of the presence, and positioning of electrodes electrically accessible from both the shown, and subject contacting sides is present. The dotted lines surrounding each of said V1, V2, V3, V4, V5 and V6 locations is to indicate that the FIGS. 5b electrode element arrangement is to be taken in combination as an electrode. Also note that FIG. 7b shows Perforations (P) present in the Support Sheet (SUP) at electrode RA, LA, and LL, (eg. Right Arm, Left Arm and Left Leg) locations. Said Perforations (P) allow easy removal of the RA, LA, and LL electrodes when it is desired to deploy and place said electrodes at conventional subject limb locations in use.

Figure 7C:
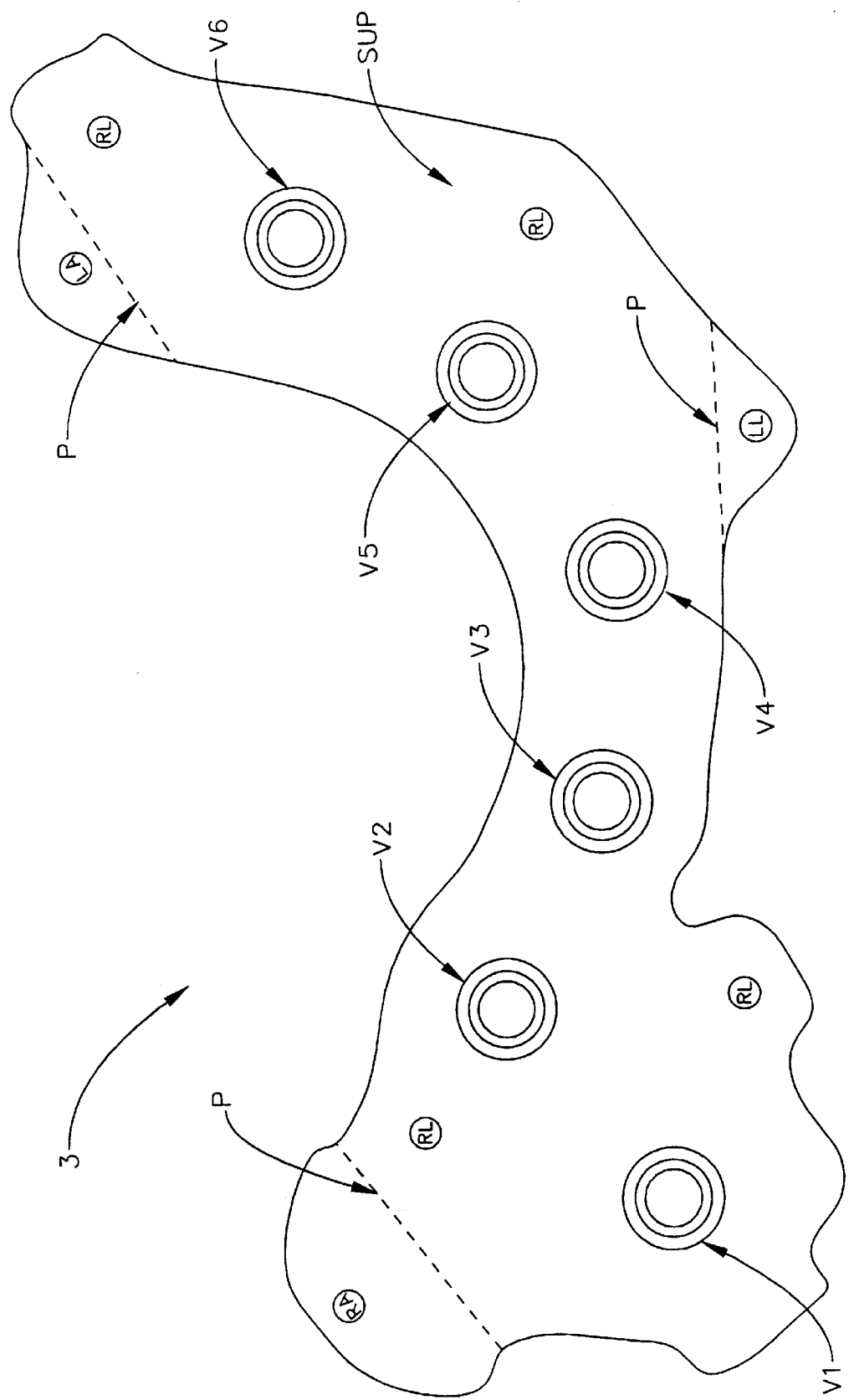
FIG. 7c shows a bioelectric interface configured for use with a twelve lead (ECG) system. Shown are groups of electrodes made of a plurality of electrode elements configured as shown in FIG. 5a, which serve to allow high frequency investigation and mapping. Shown also are perforations in a continuous support sheet for use in detaching leads used in forming an Einthoven triangle Left Arm, Right Arm and Left Leg pattern.

FIG. 7c shows a present invention Bioelectric Interface (3) with FIG. 5a Bulls-eye electrodes present at V1, V2, V3, V4, V5 and V6 locations in the Support Sheet (SUP). As in FIGS. 7a and 7b, the Bioelectric Interface is viewed from the non-subject contacting side, and indications of the presence, and positioning of electrodes electrically accessible from both the shown, and subject contacting sides is present. Also note that FIG. 7c, as did FIG. 7b, shows Perforations (P) present in the Support Sheet (SUP) at electrode RA, LA, and LL (eg. Right Arm, Left Arm and Left Leg) locations. (Said term "Perforations (P)" is to be interpreted to include functionally equivalent means which enable easy removal of the RA, LA, and LL electrodes when it is desired to deploy said electrodes at conventional limb locations in use).

Figure 7D:
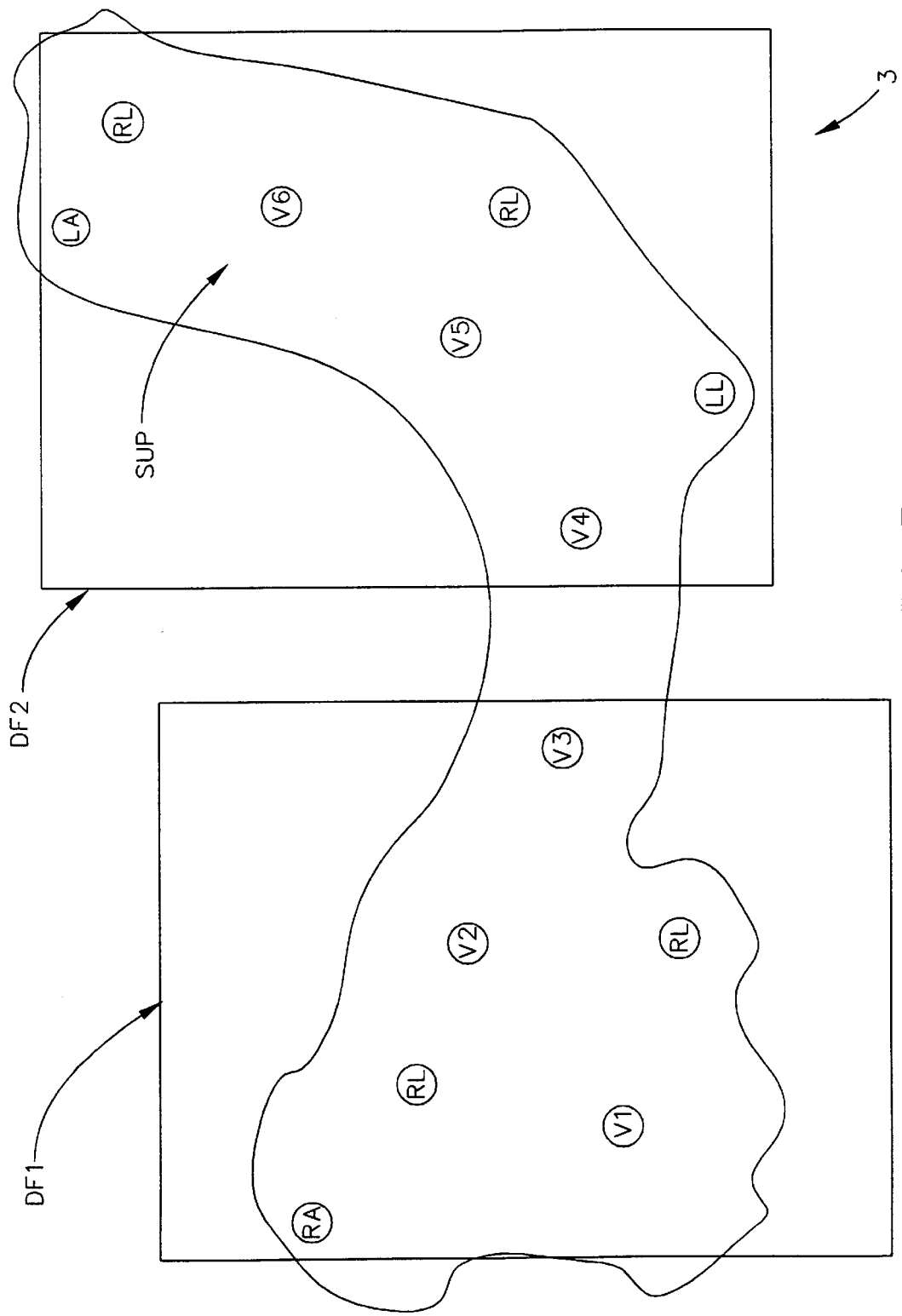
FIG. 7d shows a bioelectric interface configured for use with a twelve lead (ECG) system. Indicated are electrodes positioned beneath paddles of a defibrillating system.

FIG. 7d shows a present invention Bioelectric Interface (3) with simple single Button electrodes present at V1, V2, V3, V4, V5 and V6 locations in the Support Sheet (SUP). As in FIGS. 7a, 7b and 7c, the Bioelectric Interface is viewed from the non-subject contacting side, and indications of the presence, and positioning of electrodes electrically accessible from both the shown, and subject contacting sides is present. Also shown are outline representations of First (DF1) and Second (DF2) Defibrillation Paddles placed over the Ra, LA, LL, V1, V2, V3, V4, V5 and V6 electrodes of the present invention Bioelectric Interface (3), as said First (DF1) and Second (DF2) Defibrillation Paddles would be positioned in use. Note that First (PD1) Defibrillation Paddle electrically contacts electrodes RA, V1, V2, and V3, while Second (DF2) Defibrillation Paddle electrically contacts electrodes LA, LL, V4, V5, and V6. The multiple points of supply of electrical energy to the body of a subject wearing the present invention Bioelectric Interface (3) serves to reduce uneven current flow caused by electrode "Edge" effect. It should be appreciated that were First (DF1) and Second (DF2) Defibrillation Paddles shown applied to FIGS. 7b or 7c, even more separate electrode elements would be contacted, and the "Edge" effect would be even more reduced.

Figure 7E:
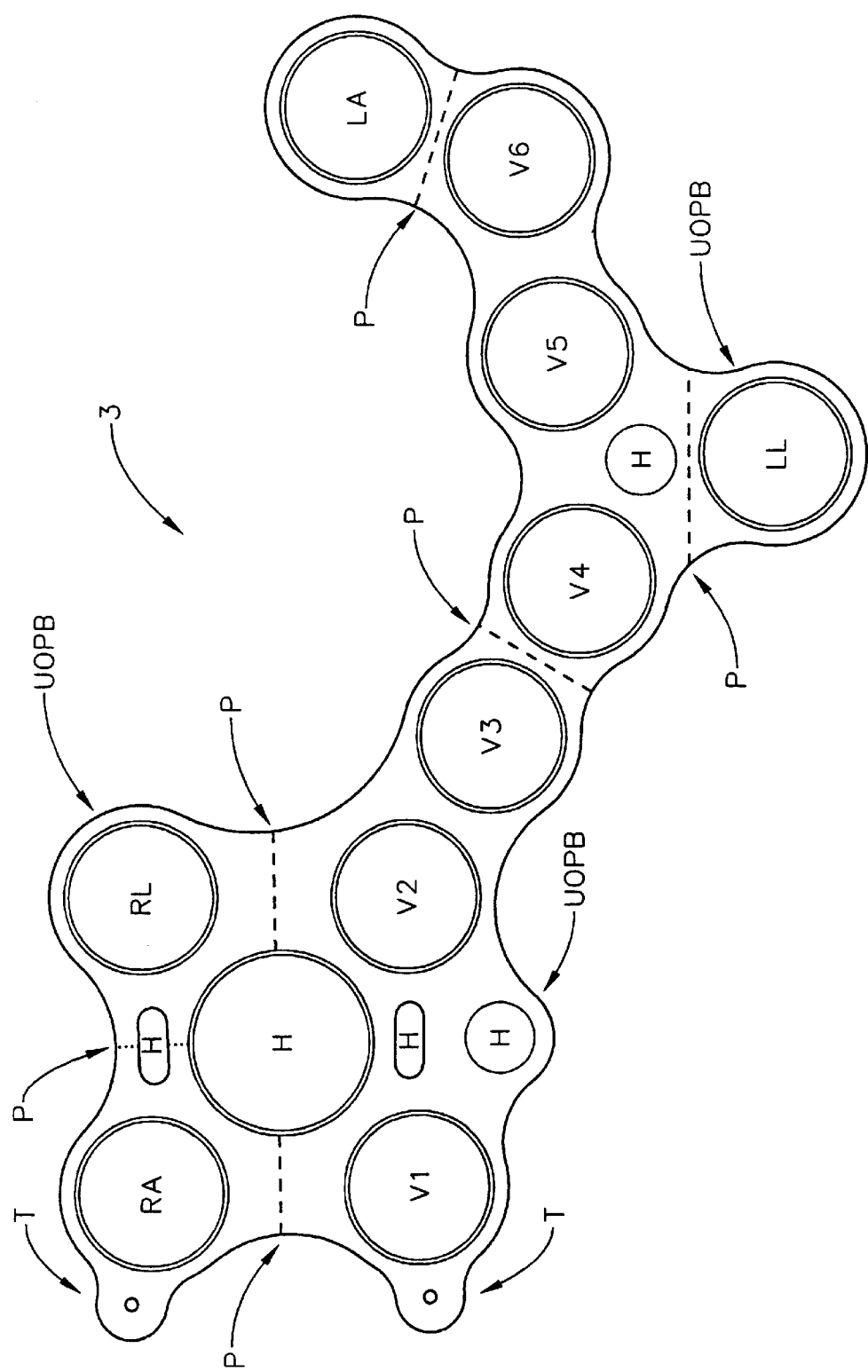
FIG. 7e shows a bioelectric interface with an undulated curved tab shaped outer edge, in combination with the presence of strategically placed holes through said bioelectric interface.
Figure 7F:
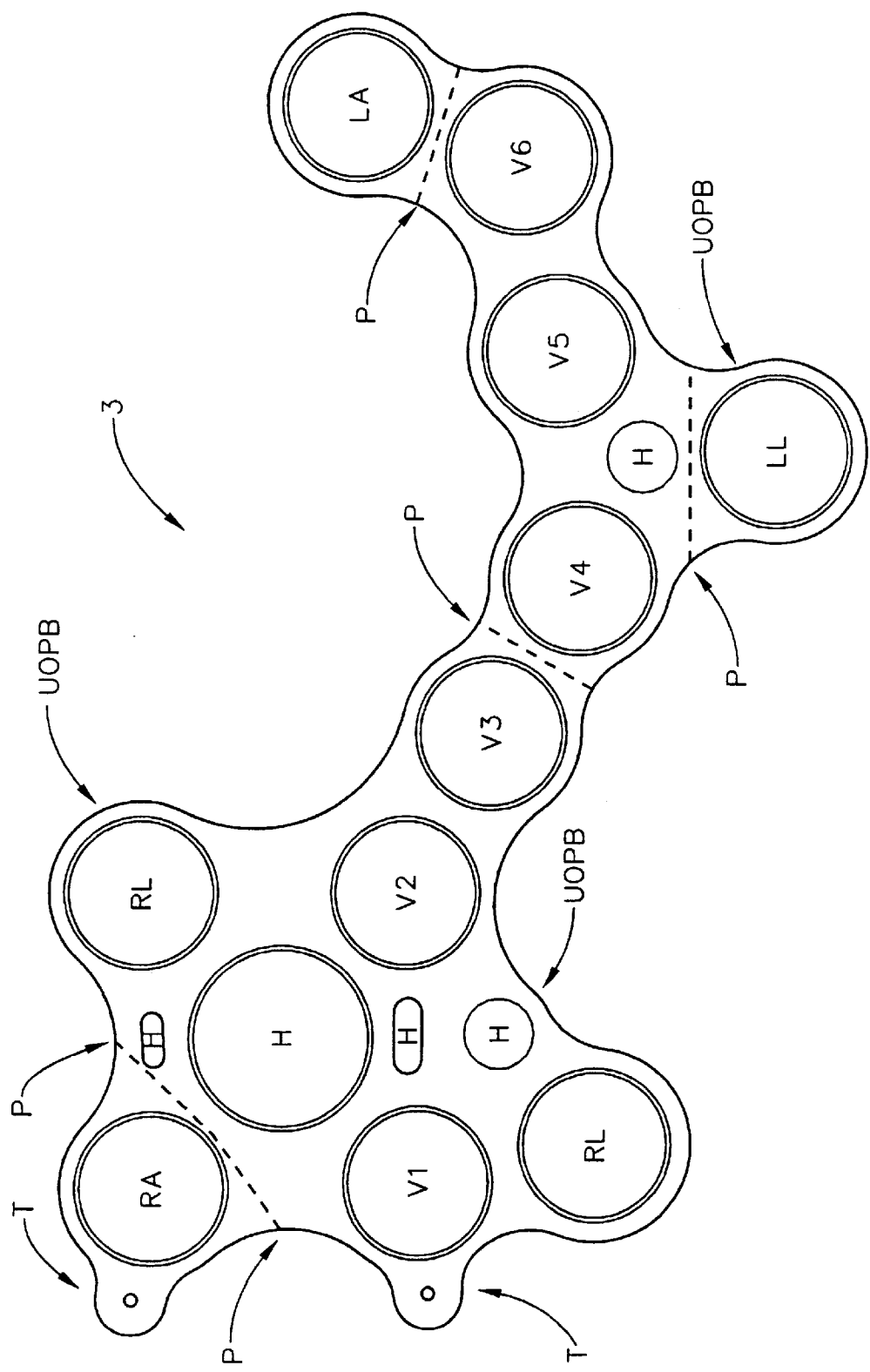
FIG. 7f shows a variation of FIG. 7e, in which the Right Leg (RL) electrode is positioned in an automatically more familiar location.

Turning now to FIG. 7e, there is shown a prefered embodiment of the present invention bioelectric interface (3). Shown are a support sheet (SUP) in functional combination with at least nine (9) spatially separated electrocardiogram system electrodes, each of said at least nine (9) spatially separated electrocardiogram system electrodes, which can be of a construction selected from a group consisting of: (a single electrical electrode element and a group of electrically independent electrode elements). Each of said spatially separated electrocardiogram system electrodes is affixed to said support sheet (SUP) in a manner such that the relative positions of said electrocardiogram system electrodes with respect to one another are essentially fixed therewithin. Nine (9) of said at least nine (9) electrocardiogram system electrodes are configured in an RA, LA, LL, V1, V2, V3, V4, V5, V6 electrocardiogram system electrode pattern much as described with respect to FIGS. 7a–7d. The prefered embodiment is shown to also include an electocardiogram system RL electrode. In particular it should be noted that the FIG. 7e embodiment further comprises perforations in said support sheet (SUP) which allow easy detachment and deployment of at least one of said electrocardiogram RA, LA, LL and RL electrodes, thereby allowing positioning at a location selected from the group consisting of: (in contact with a subject's chest, and in conventional subject limb position). Further note that fold enhancing impression and/or perforations are shown as present invention V3 and V4 electrodes, and between RA and V1 electrodes. Such fold enhancing impression and/or perforations can be present between essentially any at two electrodes such as between V1 and V2; V2 and V3; V3 and V4; V4 and V5; V5 and V6; RA and V1; V4 and LL; LA and V6. As with other embodiments in said FIG. 7e prefered embodiment, the support sheet is at least partially covered with an adhesive material on a subject contacting side thereof, and said adhesive material can present with electrical conductive properties selected from the group consisting of: (isotropic electrical conductive properties, and anisotropic electrical conductive properties such that the regional specific impedance through said adhesive material is less than in a laterally oriented dimension direction therealong). Also, said adhesive material can be hydrophillic and non-hydrophillic and partially hydrophillic and partially htdrophobic. Note also that the bioelectric interface in FIG. 7e has at least one hole (H) present through said support sheet at a location between electrodes, which hole allows access to a subject's skin in use. Holes (H) are shown at location of the level of the second intercostal space adjacent to said RA electrode, and at the level of the fourth intercostal space adjacent to said V1 electrode, and between said RA and V2 electrodes, and between said V4 and V5 electrodes. Such holes make the bioelectric interface more compliant and able to conform to a subject's body contours. Also note that the FIG. 7e bioelectric interface has an "undulated" outer perimeter boundary shape. This is prefered at it further enhances conformation to a subject's body contours in use, and said "undulations" allow relatively easy grasping between a thumb and first finger, thereby facilitating removal of a bioelectric interface from a subject, (which has proven a bit difficult with some bioelectric interfaces without an "undulated" outer perimeter boundary. FIG. 7f shows a variation of FIG. 7e, in which the Right Leg (RL) electrode is positioned in an anatomically more familiar location. It is noted however, that the Right Leg (RL) electrode is utilized only for entering noise cancelling signals, hence can be located essentially anywhere in the bioelectric interface (3).

As a general comment regarding FIGS. 7a, 7b, 7c, 7d, 7e and 7f, the electrodes are shown positioned in each Bioelectric Interface (3), as viewed from the non-subject contacting side thereof. FIG. 4c demonstrates the typically only an external device electrical connector means (EC) is visible as so viewed, with a typically larger electrode area present on the subject contacting side. Hence, FIGS. 7a, 7b, 7c, 7d, 7e and 7f should be viewed as demonstrating the positioning of electrodes, and elements which comprise them, in a present invention Bioelectric Interface, rather than being accurate representations of the size of said electrodes, as viewed.

As another general comment, it is to be appreciated that the present invention bioelectric interface system provides a means by which many electrodes can be applied to a subject by a simple, error limiting procedure. As it is generally accepted that improper application of electrodes is the most common reason for faulted (ECG) data acquisition, this is significant. As well, the present invention bioelectric interface provides a rather significant body contact surface area, said surface area being, typically, essentially covered with an adhesive material. This serves to ensure that electrodes, once applied to a subject, will not vary from the positions in which they are applied, and should not vary with respect to one another. It is known that relative motion between electrodes accounts for production of noise in acquired (ECG) data. The present invention greatly limits problems associated with noise generated by this effect. In fact, it is generally possibly to perform cardio-pulmonary-resuscitation on subjects wearing the present invention bioelectric interface while continuing to acquire (ECG) data. It is also mentioned that when the adhesive material is a hydropolymer, subject discomfort is minimized, and moisture resulting from sweating etc. actually serves to improve the adhesion properties.

While not shown, it is possible to form arrays of electrodes in a present invention bioelectric interface, for use in cardiac mapping. In such arrays, electrode arrangement is typically rectangular with, for instance, sixteen, twenty-four, thirty-six, sixty-four etc. electrodes present. The electrodes present can be of Button or Bulls-eye geometry, or, in other embodiment of the present invention, can be of any functional geometrical shape. It is also noted that it is possible to affix alternative embodiments of the present invention bioelectric interface to the back of a subject as well as to the chest thereof.

It is also noted that primary evidence that a Wilson Common Terminal (WCT) Voltage produced utilizing a present invention Bioelectric Interface is equivalent, (eg. within some selected range of deviation from), to that produced when conventionally placed limb leads are utilized, is essential equivalence of monitored ECG lead outputs from both said systems. In that light it is to be understood that a conventional Wilson Common Terminal is constructed utilizing resistors of equal value, (eg. 10,000 ohms each). Again refering to FIGS. 6a and 6b, this is equivalent to considering Resistors (r1), (r2) and (r3) to be of equivalent values. Where this is the case, placement of the Right Arm (RA), Left Arm (LA) and Left Leg (LL) electrodes alone, in a FIG. 6b setting, provides for realizing a voltage at the FIG. 6b Wilson Common Terminal (WCT) which is in a desired relationship to that present at the Wilson Common Terminal (WCT) formed utilizing electrodes positioned on limbs, as shown in FIG. 6a. However, it should be appreciated that if resistors/impedances (r1), (r2) and (r3) are variable, then adjusting their values can also have an effect on the voltage which appears at a Wilson Common Terminal (WCT). The present invention provides for use of variable (r1) and/or (r2) and/or (r3) resistor(s) such that in use, adjustment of one or more of said variable (r1) and/or (r2) and/or (r3) resistor(s) allows "setting" a voltage at the Wilson Common Terminal (WCT) to essentially any value at, or anywhere between, the voltages present at any of the Right Arm (RA), Left Arm (LA) and Left Leg (LL) electrodes. Thus, the present invention can include as a Method of Use step, adjustment of the values of the resistors which form the Wilson Common Terminal (WCT), after a FIG. 6b Bioelectric Interface (3) is placed upon a subject's chest. (Note that Operational Amplifiers with adjustable gain can be utilized in place of the described variable resistors and are to be considered functionally equivalent and within the scope of the terminology "variable resistor". Op-Amps beneficially provide high input impedance.)

It will be apparent to those skilled in the art that some redundancy exists in any Einthoven-like lead system which lies largely in a single subject body plane, such as the frontal plane. Some minor efficiencies might be achieved, at the expense of redundance, if for example, two mutually perpendicular leads were created and used exclusively to define the frontal plane in electrocardiology. Furthermore, other mathematically derived leads are commonly employed to provide additional information, (eg "augmented" frontal plane leads). However, it is to be understood that new heart related information can not be created simply by the mathematical manipulation of redundant information. Therefore, where appropriate, this disclosure is to be interpreted to include mathematically equivalent lead placement systems. In particular, the language, "generally in the region of" should be interpreted sufficiently broadly to include both an Einthoven equivalent triangle and an orthogonal lead configuration formed by a shifting of a lead position, which identified lead configurations provide mathematically essentially equivalent information.

It is specifically stated, as it is difficult to otherwise describe, that for the purposes of this disclosure the term "undulate" is defined as indicating a sequential plurality of curves in said bioelectric interface "undulated" outer perimeter boundary (UOPB), as shown in FIGS. 7e and 7f. This is best understood by comparison to a bioelectric interface outer perimeter boundary with a relatively "smoothed" shape, as is shown in FIGS. 7a–7d.

Figure 8:
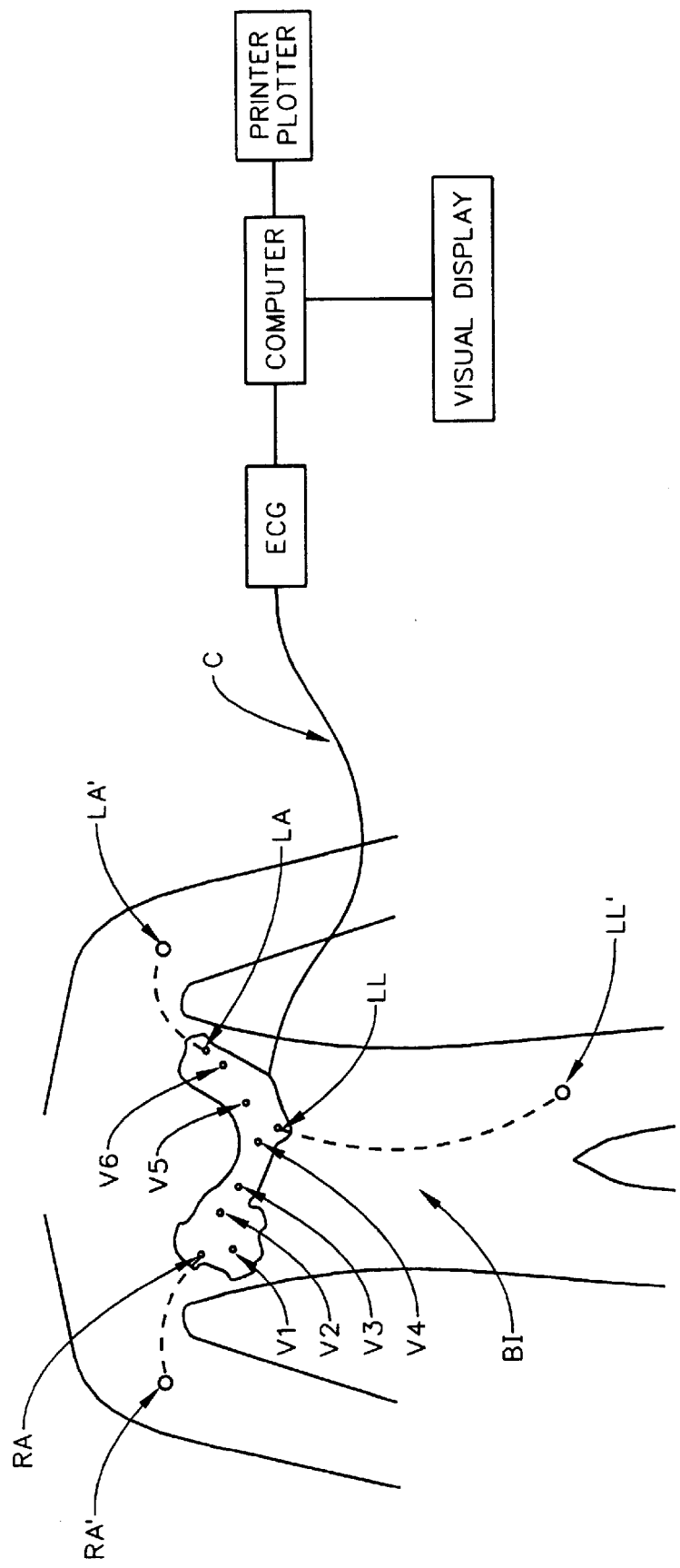
FIG. 8 generally exemplifies a system for utilizing an electrode patch (3) as shown in FIGS. 7a–7f. A computer system is shown situated to receive an (ECG) signal, and based thereupon cause a control system identified as (PACE/DEFIB) to provide electrical impulses to a subject via said electrode patch (3).

In keeping with the Method theme of the present invention as described in the Disclosure of the Invention Section herein, FIG. 8 generally exemplifies a system for utilizing an electrode patch (3) as shown in FIGS. 7a–7f. A computer system is shown situated to receive subject (ECG) and Upper Torso Impedance Interrrogation signals, and based thereupon cause a control system identified as (PACE/DEFIB) to provide electrical impulses to a subject via said electrode patch (3). The (PACE/DEFIB) control system provides logic, voltage and switchable impedance source means to perform the method recited in the Disclosure of the Invention Section of this Specification. Specifically, it is to be appreciated that resistors can be attached to any of the RA, LA, LL, V1, V2, V3, V4, V5, V6 electrodes via said (PACE/DEFIB) control system, for the purpose of applying controlled theraputic voltages therethrough, in use.

It is further noted that where FIG. 7d Defibrillation Paddles ((DF1) and (DF2) in FIG. 7d) are placed in contact with groups of electrodes, and it can happen that electrodes can be project to different heights above an OMNITRODE (3) when it is placed on a subject, (see FIG. 9b). FIG. 9a shows that an Electrode (CM) above a Subject Contacting aspect (EL) can be constucted to include Spring Means (S) with a Piston-type (PL) contact present at an upper aspect. FIG. 9b shows the electrical contact enhancing action of a plurality of such Electrodes (CM1), (CM2) and (CM3) when a Defibrillation Paddle (DFP) is simultaneously placed thereonto. Thus, the present invention includes FIGS. 9a and 9b electrode contacting enhancing means.

Finally, it is noted that the terminology "Wilson Common Terminal" has been used in this Disclosure, whereas many references utilize the terminology "Wilson Central Terminal". The term "Common" is used to imply application in an instrumentation setting, but for most purposes it can be read as "Central" without loss of accuracy.

Having hereby disclosed the subject matter of the present invention, it should be obvious that many modifications, substitutions, and variations of the present teachings are possible in view of the teachings. It is therefore to be understood that the present invention may be practiced other than as specifically described, and should be limited in breadth and scope only by the claims.

I claim:

1. A bioelectric interface comprising an adhesive sheet in functional combination with at least two spatially separated electrodes, which adhesive sheet simultaneously presents with essentially anisotropic specific impedance properties and essentially isotropic mechanical pliability and adhesion properties, said electrodes being affixed to said adhesive sheet in a manner such that their relative positions with respect to one another are essentially fixed, and such that the specific impedance from each said electrode directly through said adhesive sheet, is less than that between any said electrodes through said adhesive sheet, said electrical anisotropic specific impedance properties of said adhesive sheet being the result of scrim therein, which scrim is a web of material having no electrically conductive adhesive material impregnated thereinto but having relatively electrically conductive adhesive material present in open areas of said web so as to form channel regions of electrically conductive adhesive material bordered by said scrim web material, such that electrically conductive adhesive material in one channel region does not contact that in other regions, at least one of said at least two spatially separated electrodes having a region of said scrim web material positioned thereunder, as viewed in side elevation.

2. A bioelectric interface as in claim 1, in which the adhesive sheet is comprised of electrically conductive polymer.

3. A bioelectric interface as in claim 2, in which the electrically conductive polymer is hydrophillic, and thereby particularly well suited for application to human skin.

4. A bioelectric interface as in claim 1, in which the electrodes are each of a construction such that contact with the adhesive sheet is essentially continuous over the dimension of each said electrode.

5. A bioelectric interface as in claim 1, in which at least one of said electrodes is of a multiple-piece construction such that each of said multiple pieces contacts the adhesive sheet independently and essentially continuously over the dimension of each said multiple pieces.

6. A bioelectric interface as in claim 5, in which the multipiece construction configures a Bulls-eye pattern.

7. A bioelectric interface as in claim 6, in which there are present a multiplicity of electrodes configured in an essentially rectangular shaped matrix such that in use said bioelectric interface is affixed to one of the group consisting of a patient's chest and back, said bioelectric interface being appropriate for use in electrocardiographic mapping.

8. A bioelectric interface as in claim 1, which further comprises a carrier matrix affixed thereto so as to sandwich said electrodes between said carrier matrix and said adhesive sheet, the purpose being to improve the integrity of the spacial separation between said electrodes.

9. A bioelectric interface as in claim 1, which further comprises means for electrically connecting said electrodes to external devices.

10. A bioelectric interface as in claim 1, in which there are present a multiplicity of electrodes configured in an essentially rectangular shaped matrix such that in use said bioelectric interface is affixed to one of the group consisting of a patient's chest and back, said bioelectric interface being appropriate for use in electrocardiographic mapping.

11. A bioelectric interface comprising an adhesive sheet in functional combination with at least two spatially separated regions of electrode(s), at least one of which spatially separated region of electrode(s) can consist of more than one electrode, which adhesive sheet simultaneously presents with essentially anisotropic specific impedance properties and essentially isotropic pliability and adhesion mechanical properties, electrode(s) in each of said spatially separated regions of electrode(s) being affixed to said adhesive sheet in a manner such the relative positions of electrodes present with respect to one another are essentially fixed, and such that the specific impedance from each electrode in said regions of spatially separated electrode(s) directly through said adhesive sheet, is less than that between any two electrodes in different spatially separated regions of electrode(s) through said adhesive sheet, said electrical anisotropic specific impedance properties of said adhesive sheet being the result of at least one selection from the group consisting of:

scrim therein, which scrim is a web of material having no electrically conductive adhesive material impregnated thereinto but but having relatively electrically conductive adhesive material present in open areas of said web so as to form channel regions of electrically conductive adhesive material bordered by said scrim web material, such that electrically conductive adhesive material in one channel region does not contact that in other regions, at least one of said at least two spatially separated electrodes having a region of said scrim web material positioned thereunder, as viewed in side elevation; and slits therein, which slits are positioned between electrodes.

12. A bioelectric interface as in claim 11, in which the adhesive sheet is comprised of electrically conductive polymer.

13. A bioelectric interface as in claim 12, in which the electrically conductive polymer is hydrophillic, and thereby particularly well suited for application to human skin.

14. A bioelectric interface as in claim 11, in which the electrodes in the regions of electrode(s) are each of a construction such that contact with the adhesive sheet is essentially continuous over the dimension of each said electrode.

15. A bioelectric interface as in claim 11, in which at least one of said electrodes in said regions of electrode(s) is of a multiple-piece construction such that each of said multiple pieces contacts the adhesive sheet independently and essentially continuously over the dimension of each said multiple pieces.

16. A bioelectric interface as in claim 15, in which the multipiece construction configures a Bulls-eye pattern.

17. A bioelectric interface as in claim 11, which further comprises a carrier matrix affixed thereto so as to sandwich said electrodes in said regions of electrode(s) between said carrier matrix and said adhesive sheet, the purpose being to improve the integrity of the spatial separation between said electrodes.

18. A bioelectric interface as in claim 11, which further comprises means for electrically connecting said electrodes in said regions of electrode(s) to external devices.

19. A bioelectric interface as in claim 11, in which the number of regions of electrode(s) is three, said bioelectric interface being configured and sized so as to place said three regions of electrodes in an essentially congruent Einthoven triangle Left Arm, Right Arm, Left Leg pattern, such that in use all said regions of electrodes contact a patient's chest.

20. A bioelectric interface as in claim 11, in which the number of regions of electrode(s) is nine, said nine regions of electrode(s) being configured in an RA, LA, LL, V1, V2, V3, V4, V5, V6 twelve lead electrocardiogram system electrode pattern, such that said nine regions of electrode(s) are positioned on a patient's chest during use as follows:

electrode region RA generally in the region of the second intercostal space to the right of the sternum;

electrode region LA generally in the region of the left fourth intercostal space at the mid-axillary line;

electrode region LL generally in the region of the inferior costal margin in the left mid-clavicular line;

electrode region V1 in the region of the fourth intercostal space at the right sternal border;

electrode region V2 in the region of the fourth intercostal space at the left sternal border;

electrode region V4 in the region of the fifth intercostal space at the left mid-clavicular line;

electrode region V3 in the region of the midpoint between electrode regions V2 and V4;

electrode region V5 in the region of the fifth intercostal space in the left anterior axillary line; and electrode region V6 in the region of the fifth intercostal space in the mid-axillary line.

21. A bioelectric interface as in claim 11, which comprises three regions of electrode(s) which are configured and sized so as to place electrode(s) in said three regions of electrodes in an Einthoven triangle Left Arm, Right Arm, Left Leg pattern, such that in use all said regions of electrodes contact a patient's chest as verified by the appearance of a voltage at a Wilson central terminal formed by attaching impedances from electrodes in each of said three regions of electrode(s) in a "Y" configuration which is within some selected deviation from a voltage which would appear at a Wilson central terminal formed by attaching impedances from electrodes affixed to conventional RA, LA and LL into a "Y" configuration.

22. A method of acquiring electrocardiographic data comprising the steps of:

a. providing a bioelectric interface comprising an adhesive sheet in functional combination with at least two spatially separated separated regions of electrode(s), at least one of which spatially separated region of electrode(s) can consist of more than one electrode, which adhesive sheet presents with essentially anisotropic specific impedance properties but essentially isotropic mechanical properties, said spatially separated regions of electrode(s) being affixed to said adhesive sheet in a manner such that their relative positions with respect to one another remain essentially fixed, and such that the specific impedance from each electrode in said regions of spatially separated electrode(s) directly through said adhesive sheet, is less than that between any two electrodes in different spatially separated regions of electrodes through said adhesive sheet, said electrical anisotropic specific impedance properties of said adhesive sheet being the result of at least one selection from the group consisting of:

scrim therein, which scrim is a web of material having no electrically conductive adhesive material impregnated thereinto but but having relatively electrically conductive adhesive material present in open areas of said web so as to form channel regions of electrically conductive adhesive material bordered by said scrim web material, such that electrically conductive adhesive material in one channel region does not contact that in other regions, at least one of said at least two spatially separated electrodes having a region of said scrim web material positioned thereunder, as viewed in side elevation; and slits therein, which slits are positioned between electrodes;

in which bioelectric interface the number of regions of electrode(s) is nine, said nine regions of electrode(s) being configured in an RA, LA, LL, V1, V2, V3, V4, V5, V6 twelve lead electrocardiogram system electrode pattern, such that at least some of said nine regions of electrode(s) are positioned on a patient's chest during use as follows:

electrode region RA generally in the region of the second intercostal space to the right of the sternum;

electrode region LA generally in the region of the left fourth intercostal space at the mid-axillary line;

electrode region LL generally in the region of the inferior costal margin in the left mid-clavicular line;

electrode region V1 in the region of the fourth intercostal space at the right sternal border;

electrode region V2 in the region of the fourth intercostal space at the left sternal border;

electrode region V4 in the region of the fifth intercostal space at the left mid-clavicular line;

electrode region V3 in the region of the midpoint between electrode regions V2 and V4;

electrode region V5 in the region of the fifth intercostal space in the left anterior axillary line; and electrode region V6 in the region of the fifth intercostal space in the mid-axillary line;

b. affixing said bioelectric interface to a patient and causing the electrodes therein to be electrically attached to an electrocardiographic system such that electrocardiographic data is obtained.

23. A method of acquiring electrocardiographic data as in claim 22, which further comprises the step of performing a procedure selected from the group consisting of;

a. cardio-pulmonary resuscitation b. cardiac defibrillation;

c. cardiac pacing; and d. electro surgery, on said patient without removing said bioelectric interface.

24. A method of acquiring electrocardiographic data as in claim 22, which further comprises the step of causing at least some of said electrodes to have multiple component configuration.

25. A method of performing cardiac mapping comprising the steps of:

a. providing a bioelectric interface comprising an adhesive sheet in functional combination with at least two spatially separated electrodes, which adhesive sheet presents with essentially anisotropic specific impedance properties but essentially isotropic mechanical properties, said electrodes being affixed to said adhesive sheet in a manner such that their relative positions with respect to one another remain essentially fixed, and such that the specific impedance from each said electrode directly through said adhesive sheet, is less than that between any said electrodes through said adhesive sheet, said electrical anisotropic specific impedance properties of said adhesive sheet being the result of at least one selection from the group consisting of:

scrim therein, which scrim is a web of material having no electrically conductive adhesive material impregnated thereinto but having relatively electrically conductive adhesive material present in open areas of said web so as to form channel regions of electrically conductive adhesive material bordered by said scrim web material, such that electrically conductive adhesive material in one channel region does not contact that in other regions, at least one of said at least two spatially separated electrodes having a region of said scrim web material positioned thereunder, as viewed in side elevation; and slits therein, which slits are positioned between electrodes;

in which bioelectric interface there are present a multiplicity of electrodes configured in an essentially rectangular shaped matrix such that in use said bioelectric interface is affixed to one of the group consisting of a patient's chest and back, said bioelectric interface being appropriate for use in electrocardiographic mapping;

b. affixing said bioelectric interface to a patient's on one of the elements in the group consisting of a patient's chest and back, and causing said electrodes to be connected to an electrocardiograph mapping system.

26. A method of acquiring electrocardiographic data as in claim 25, which further comprises the step of performing a procedure selected from the group consisting of;

a. cardio-pulmonary resuscitation b. cardiac defibrillation;

c. cardiac pacing; and d. electro surgery.

27. A method of acquiring electrocardiographic data as in claim 25, which further comprises the simultaneous step of causing at least some of said electrodes to have a multiple component configuration.

\* \* \* \* \*